United States Patent
Fukumoto et al.

(10) Patent No.: US 12,057,151 B2
(45) Date of Patent: Aug. 6, 2024

(54) FLUORINE-CONTAINING ETHER COMPOUND, LUBRICANT FOR MAGNETIC RECORDING MEDIUM, AND MAGNETIC RECORDING MEDIUM

(71) Applicant: Resonac Corporation, Tokyo (JP)

(72) Inventors: Naoya Fukumoto, Ichihara (JP); Tsuyoshi Kato, Ichihara (JP); Katsumi Murofushi, Tokyo (JP); Daisuke Yagyu, Ichihara (JP); Masaki Nanko, Ichihara (JP); Natsumi Shibata, Ichihara (JP)

(73) Assignee: Resonac Corporation, Tokyo (JP)

( * ) Notice: Subject to any disclaimer, the term of this patent is extended or adjusted under 35 U.S.C. 154(b) by 38 days.

(21) Appl. No.: 17/788,125

(22) PCT Filed: Dec. 16, 2020

(86) PCT No.: PCT/JP2020/046949
§ 371 (c)(1),
(2) Date: Jun. 22, 2022

(87) PCT Pub. No.: WO2021/131961
PCT Pub. Date: Jul. 1, 2021

(65) Prior Publication Data
US 2023/0120626 A1  Apr. 20, 2023

(30) Foreign Application Priority Data
Dec. 23, 2019 (JP) ................................. 2019-232037

(51) Int. Cl.
*G11B 5/725* (2006.01)
*C07C 43/13* (2006.01)
(Continued)

(52) U.S. Cl.
CPC .......... *G11B 5/7257* (2020.08); *C07C 43/137* (2013.01); *C07C 255/13* (2013.01);
(Continued)

(58) Field of Classification Search
CPC ............... G11B 5/7257; C10M 107/38; C10M 2213/043; C10M 2213/0606;
(Continued)

(56) References Cited

U.S. PATENT DOCUMENTS 8,518,564 B2  8/2013 Burns et al.
8,734,966 B2  5/2014 Sagata
(Continued)

FOREIGN PATENT DOCUMENTS

CN  101868521 A  10/2010
CN  102356431 A  2/2012
(Continued)

OTHER PUBLICATIONS

International Search Report of PCT/JP2020/046949 dated Feb. 16, 2021 [PCT/ISA/210].
(Continued)

*Primary Examiner* — Holly Rickman
(74) *Attorney, Agent, or Firm* — Sughrue Mion, PLLC

(57) ABSTRACT

There is provided a fluorine-containing ether compound represented by the following formula. $R^1-R^2-CH_2-R^3-CH_2-OCH_2CH(OH)CH_2O-CH_2-R^3-CH_2-R^4-R^5$ (in the formula, $R^3$ represents a perfluoropolyether chain; $R^2$ and $R^4$ represent a divalent linking group having a polar group and may be the same or different from each other; $R^1$ and $R^5$ represent a terminal group bonded to an oxygen atom of $R^2$ or $R^4$ and may be the same or different from each other; and at least one of $R^1$ and $R^5$ is an organic group having 1 to 8 carbon atoms and at least one of hydrogens included in the organic group is substituted by a cyano group).

16 Claims, 1 Drawing Sheet

(51) Int. Cl.
*C07C 255/13* (2006.01)
*C10M 107/38* (2006.01)
*C10M 105/56* (2006.01)
*C10M 105/72* (2006.01)
*C10N 20/04* (2006.01)
*C10N 40/18* (2006.01)
*C10N 50/00* (2006.01)

(52) U.S. Cl.
CPC ........ *C10M 107/38* (2013.01); *C10M 105/56* (2013.01); *C10M 105/72* (2013.01); *C10M 2215/16* (2013.01); *C10M 2219/102* (2013.01); *C10N 2020/04* (2013.01); *C10N 2040/18* (2013.01); *C10N 2050/025* (2020.05)

(58) Field of Classification Search
CPC .......... C10N 2030/06; C10N 2050/025; C10N 2020/04; C10N 2040/18; C08G 65/333; C07C 43/137
See application file for complete search history.

(56) References Cited

U.S. PATENT DOCUMENTS

| | | | |
|---|---|---|---|
| 9,805,755 | B1 | 10/2017 | Yang |
| 11,292,979 | B2 | 4/2022 | Yamaguchi et al. |
| 11,332,656 | B2 | 5/2022 | Al-Yami et al. |
| 11,820,742 | B2 | 11/2023 | Fukumoto et al. |
| 2010/0233513 | A1 | 9/2010 | Imai et al. |
| 2012/0251873 | A1 | 10/2012 | Miyawaki et al. |
| 2015/0235664 | A1 | 8/2015 | Deng et al. |
| 2017/0260472 | A1 | 9/2017 | Sagata et al. |
| 2017/0337945 | A1 | 11/2017 | Nakamura et al. |
| 2018/0127543 | A1 | 5/2018 | Watanabe et al. |
| 2019/0237101 | A1 | 8/2019 | Lu et al. |
| 2019/0352573 | A1 | 11/2019 | Hatta et al. |
| 2019/0382675 | A1 | 12/2019 | Fukumoto et al. |
| 2019/0382676 | A1 | 12/2019 | Yamaguchi et al. |
| 2020/0002640 | A1 | 1/2020 | Lu et al. |
| 2020/0283392 | A1 | 9/2020 | Kato et al. |
| 2021/0188766 | A1 | 6/2021 | Nanko et al. |

FOREIGN PATENT DOCUMENTS

| | | | |
|---|---|---|---|
| CN | 108698967 | A | 10/2018 |
| EP | 3225612 | A1 | 10/2017 |
| JP | 10-143838 | A | 5/1998 |
| JP | 2009-211765 | A | 9/2009 |
| JP | 2010-143855 | A | 7/2010 |
| JP | 2010-248463 | A | 11/2010 |
| JP | 4632144 | B2 | 2/2011 |
| JP | 2012-7008 | A | 1/2012 |
| JP | 2012-184339 | A | 9/2012 |
| JP | 2014-509677 | A | 4/2014 |
| JP | 5786047 | A | 9/2015 |
| JP | 5789710 | B1 | 10/2015 |
| JP | 2018-076404 | A | 5/2018 |
| WO | 2012/170009 | A2 | 12/2012 |
| WO | 2013/054393 | A1 | 4/2013 |
| WO | 2015/022781 | A1 | 2/2015 |
| WO | WO-2015022871 | A1 * | 2/2015 ........... C07C 43/137 |
| WO | 2016/084781 | A1 | 6/2016 |
| WO | 2016/098811 | A1 | 6/2016 |
| WO | 2017/145995 | A1 | 8/2017 |
| WO | 2017/146995 | A1 | 8/2017 |
| WO | WO-2017145995 | A1 * | 8/2017 ............. C07C 43/13 |
| WO | 2018/139058 | A1 | 8/2018 |
| WO | 2018/139174 | A1 | 8/2018 |
| WO | 2019/039200 | A1 | 2/2019 |
| WO | 2019/054148 | A1 | 3/2019 |
| WO | 2019/087548 | A1 | 5/2019 |

OTHER PUBLICATIONS

Zhang et al., "Performances of Lubricants in Hard Disk and Their Influences on Dynamic Characteristics of Magnetic Recording System", Acta Tribology, 2004, vol. 24, No. 5, pp. 476-482 (7 pages total).
First Office Action dated Nov. 16, 2020, from The China National Intellectual Property Administration in Application No. 201780012549.4.
International Search Report for PCT/JP2017/006182 dated Apr. 18, 2017 [PCT/ISA/210].
International Search Report for PCT/JP2017/042189 dated Feb. 27, 2018 [PCT/ISA/210].
International Search Report for PCT/JP2021/021558 dated Aug. 3, 2021 (PCT/ISA/210).
Non-Final Office Action issued Aug. 20, 2021 in U.S. Appl. No. 15/999,837.
Non-Final Office Action issued Aug. 23, 2021 in U.S. Appl. No. 16/470,713.
Non-Final Office Action issued Mar. 29, 2021 in U.S. Appl. No. 15/999,837.
X.-C. Guo, et al., "A multidentate lubricant for use in hard disk drives at sub-nanometer thickness", vol. 111, Journal of Applied Physics, 2012, 024503-1 to 024503-7 (7 pages total).
Non-Final Office Action issued Sep. 27, 2023 in U.S. Appl. No. 18/009,221.
Non-Final Office Action issued Feb. 28, 2024 in U.S. Appl. No. 18/009,221.
International Search Report for PCT/JP2020/047070 dated Feb. 16, 2021 [PCT/ISA/210].
Non-Final Office Action issued Mar. 15, 2023 in U.S. Appl. No. 17/788,169.
Notice of Allowance issued Jan. 28, 2022 in U.S. Appl. No. 16/470,713.
Notice of Allowance issued Dec. 15, 2021 in U.S. Appl. No. 15/999,837.
Notice of Allowance issued Jul. 12, 2023 in U.S. Appl. No. 17/788,169.

* cited by examiner

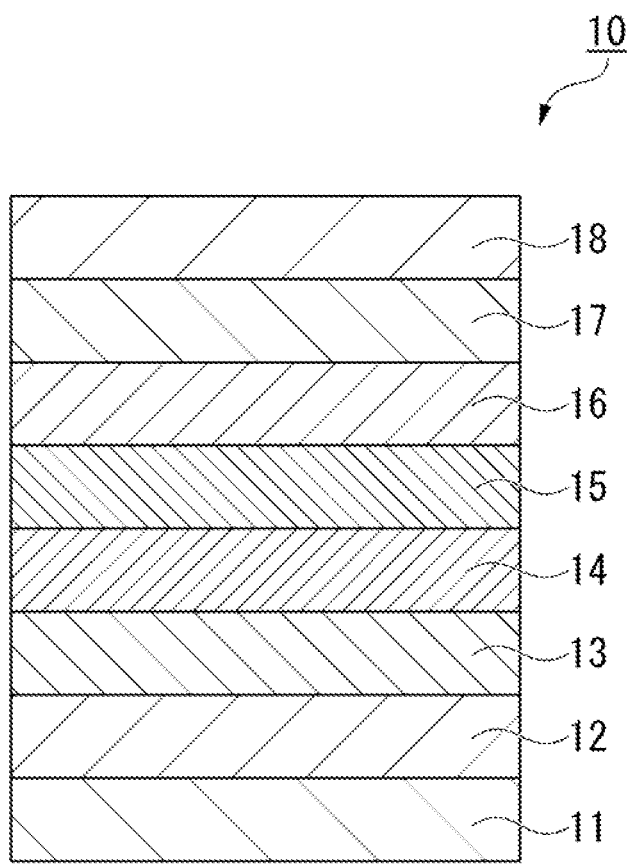

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2020/046949, filed Dec. 16, 2020, claiming priority to Japanese Patent Application No. 2019-232037, filed Dec. 23, 2019, the contents of all of which are incorporated herein by reference in their entirety.

TECHNICAL FIELD

The present invention relates to a fluorine-containing ether compound, a lubricant for a magnetic recording medium and a magnetic recording medium.

BACKGROUND ART

The development of magnetic recording media suitable for high recording densities has progressed in order to improve the recording densities of magnetic recording/reproducing devices.

As a conventional magnetic recording medium, there has been a magnetic recording medium in which a recording layer is formed on a substrate and a protective layer made of carbon or the like is formed on the recording layer. The protective layer protects information recorded in the recording layer and enhances the slidability of a magnetic head. However, sufficient durability of the magnetic recording medium cannot be obtained by simply providing the protective layer on the recording layer. Therefore, generally, a lubricant is applied to the surface of the protective layer to form a lubricating layer.

As a lubricant that is used for forming a lubricating layer in a magnetic recording medium, for example, a lubricant containing a compound having a polar group such as a hydroxyl group or an amino group at a terminal of a fluorine-based polymer having a repeating structure containing $CF_2$ has been proposed.

For example, Patent Document 1 and Patent Document 2 disclose a compound in which a perfluoropolyether is bonded to both sides of an aliphatic hydrocarbon chain having a hydroxyl group present in the center of a molecule.

Patent Document 3 discloses a fluorine-containing ether compound in which a divalent linking group having a polar group is bonded to both terminals of a perfluoropolyether chain, and at least one of the divalent linking groups is bonded to a terminal group, which is an organic group having 1 to 8 carbon atoms and at least one hydrogen in the organic group is substituted by a cyano group.

CITATION LIST

Patent Literature

[Patent Document 1]
  U.S. Pat. No. 9,805,755
[Patent Document 2]
PCT International Publication No. WO 2016/084781
[Patent Document 3]
  PCT International Publication No. WO 2019/039200

Technical Problem

There is a demand for a further decrease in a floating height of a magnetic head in magnetic recording/reproducing devices. This requires a further decrease in the thickness of a lubricating layer in magnetic recording media.

However, generally, if the thickness of the lubricating layer is reduced, the adhesion of the lubricating layer is lowered, and chemical substance resistance and wear resistance of magnetic recording media tend to be lowered.

The present invention has been made in view of the above circumstances, and an object of the present invention is to provide a fluorine-containing ether compound which can form a lubricating layer having excellent adhesion and favorable chemical substance resistance and wear resistance even if the thickness is thin, and can be suitably used as a material for a lubricant for a magnetic recording medium.

In addition, another object of the present invention is to provide a lubricant for a magnetic recording medium which contains the fluorine-containing ether compound of the present invention and which can form a lubricating layer having excellent adhesion and favorable chemical substance resistance and wear resistance.

In addition, still another object of the present invention is to provide a magnetic recording medium in which a lubricating layer containing the fluorine-containing ether compound of the present invention is provided and which has excellent reliability and durability.

Solution to Problem

The present invention includes the following first aspect.

[1] A fluorine-containing ether compound represented by the following Formula (1):

(in Formula (1), $R^3$ represents a perfluoropolyether chain; $R^2$ and $R^4$ represent a divalent linking group having a polar group, and may be the same as or different from each other; $R^1$ and $R^5$ represent a terminal group bonded to an oxygen atom of $R^2$ or $R^4$, and may be the same as or different from each other; and at least one of $R^1$ and $R^5$ is an organic group having 1 to 8 carbon atoms and at least one of hydrogens included in the organic group is substituted by a cyano group).

The compound of the first aspect of the present invention preferably has the following features [2] to [13]. It is preferable to combine two or more of these features.

[2] The fluorine-containing ether compound according to [1],
  wherein the organic group is a phenyl group, or an alkyl group having 1 to 5 carbon atoms.

[3] The fluorine-containing ether compound according to any one of [1] to [2],
  wherein the polar group is a hydroxyl group.

[4] The fluorine-containing ether compound according to [3],
wherein, in Formula (1), the total number of a hydroxyl group contained in $R^2$ and a hydroxyl group contained in $R^4$ is 2 to 5.

[5] The fluorine-containing ether compound according to any one of [1] to [4],
wherein, in Formula (1), $R^2$ and $R^4$ contain 1 to 3 linking groups represented by the following Formula (2):

$$—CH_2CH(OH)CH_2— \qquad (2)$$

[6] The fluorine-containing ether compound according to [5],
wherein, in Formula (1), $R^2$ and $R^4$ are a linking group represented by the following Formula (2-1):

$$—O—X—(Y^1X)_a—Y^2— \qquad (2\text{-}1)$$

(in Formula (2-1), a represents an integer of 0 to 2; X represents Formula (2); $Y^1$ represents any one selected from the group consisting of —O—, —CH$_2$—, —CH$_2$O—, and —OCH$_2$—; and $Y^2$ represents —O— or —CH$_2$O—).

[7] The fluorine-containing ether compound according to [6],
wherein, in Formula (2-1), $Y^1$ and $Y^2$ are —O—.

[8] The fluorine-containing ether compound according to any one of [1] to [7],
wherein, in Formula (1), $R^3$ is any one selected from the group consisting of perfluoropolyether chains represented by the following Formulae (3) to (5):

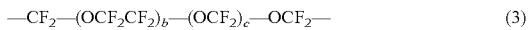

(in Formula (3), b and c indicate an average degree of polymerization, b represents 1 to 20, and c represents 0 to 20).

(in Formula (4), d indicates an average degree of polymerization, and represents 1 to 20), and

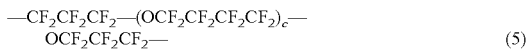

(in Formula (5), e indicates an average degree of polymerization, and represents 1 to 10).

[9] The fluorine-containing ether compound according to any one of [1] to [8],
wherein, in Formula (1), $R^1$ and $R^5$ are a phenyl group which is substituted with at least one cyano group, or an alkyl group having 1 to 5 carbon atoms which is substituted with at least one cyano group.

[10] The fluorine-containing ether compound according to any one of [1] to [9],
wherein, in Formula (1), two perfluoropolyether chains represented by $R^3$ are the same, $R^2$ and $R^4$ are the same, and $R^1$ and $R^5$ are the same.

[11] The fluorine-containing ether compound according to any one of [1] to [8],
wherein, in Formula (1), one of $R^1$ and $R^5$ is a phenyl group which is substituted with at least one cyano group, or an alkyl group having 1 to 5 carbon atoms which is substituted with at least one cyano group, and the other of $R^1$ and $R^5$ is an organic group which includes at least one selected from the group consisting of an aromatic hydrocarbon-containing group, an aromatic heterocycle-containing group, an alkenyl group, and an alkynyl group.

[12] The fluorine-containing ether compound according to [1], which is any of compounds represented by the following Formulae (A) to (P):

(A)
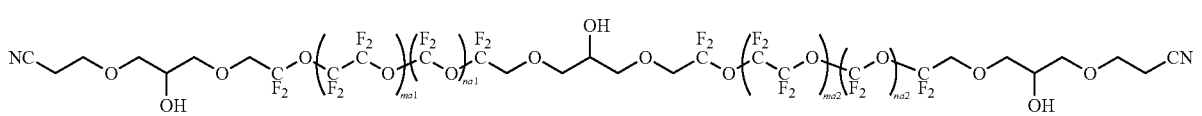

(B)
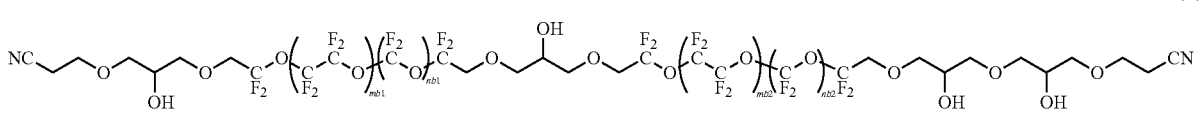

(C)
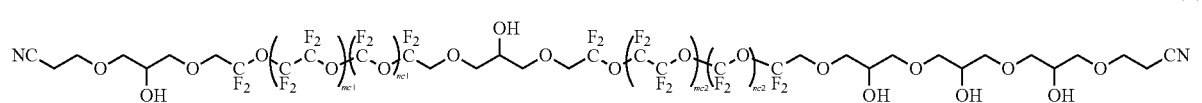

(D)
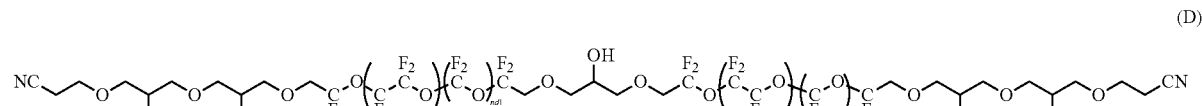

(in Formula (A), ma1, ma2, na1, and na2 indicate an average degree of polymerization, ma1 and ma2 represent 1 to 20, and na1 and na2 represent 0 to 20), (in Formula (B), mb1, mb2, nb1, and nb2 indicate an average degree of polymerization, mb1 and mb2 represent 1 to 20, and nb1 and nb2 represent 0 to 20), (in Formula (C), mc1, mc2, nc1, and nc2 indicate an average degree of polymerization, mc1 and mc2 represent 1 to 20, and nc1 and nc2 represent 0 to 20), and (in Formula (D), md1, md2, nd1, and nd2 indicate an average degree of polymerization, md1 and md2 represent 1 to 20, and nd1 and nd2 represent 0 to 20),

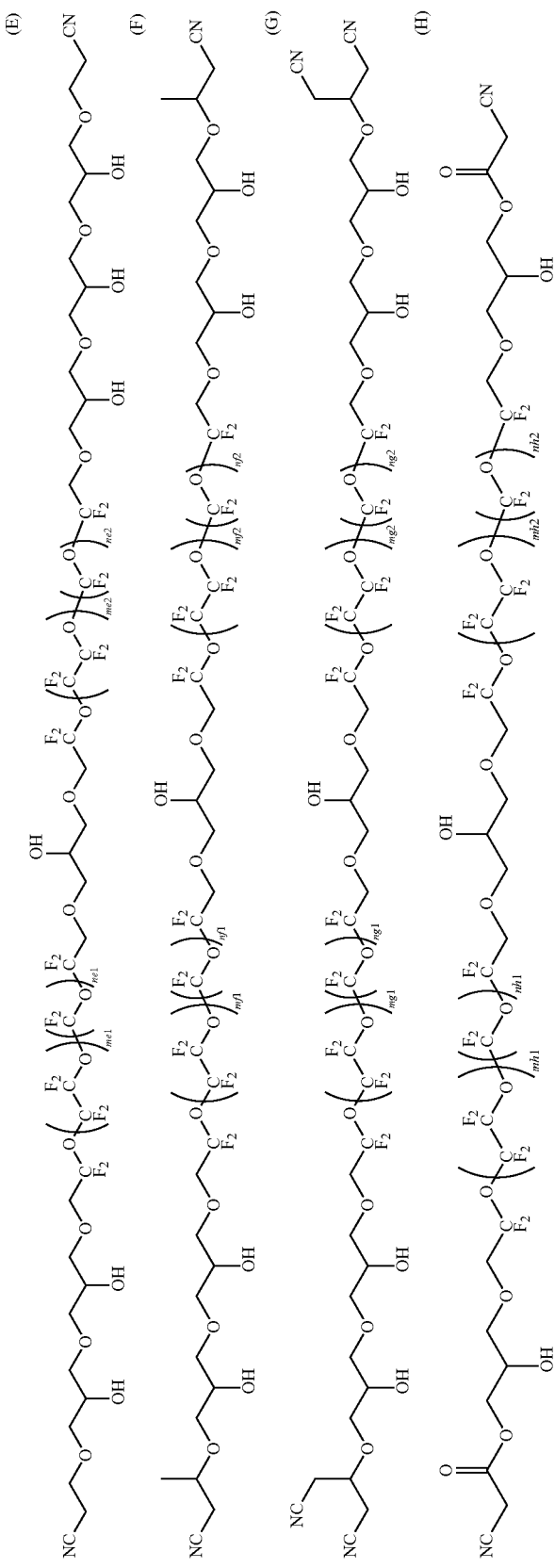

(in Formula (E), me1, me2, ne1, and ne2 indicate an average degree of polymerization, me1 and me2 represent 1 to 20, and ne1 and ne2 represent 0 to 20), (in Formula (F), mf1, mf2, nf1, and nf2 indicate an average degree of polymerization, mf1 and mf2 represent 1 to 20, and nf1 and nf2 represent 0 to 20), (in Formula (G), mg1, mg2, ng1, and ng2 indicate an average degree of polymerization, mg1 and mg2 represent 1 to 20, and ng1 and ng2 represent 0 to 20), and (in Formula (H), mh1, mh2, nh1, and nh2 indicate an average degree of polymerization, mh1 and mh2 represent 1 to 20, and nh1 and nh2 represent 0 to 20),

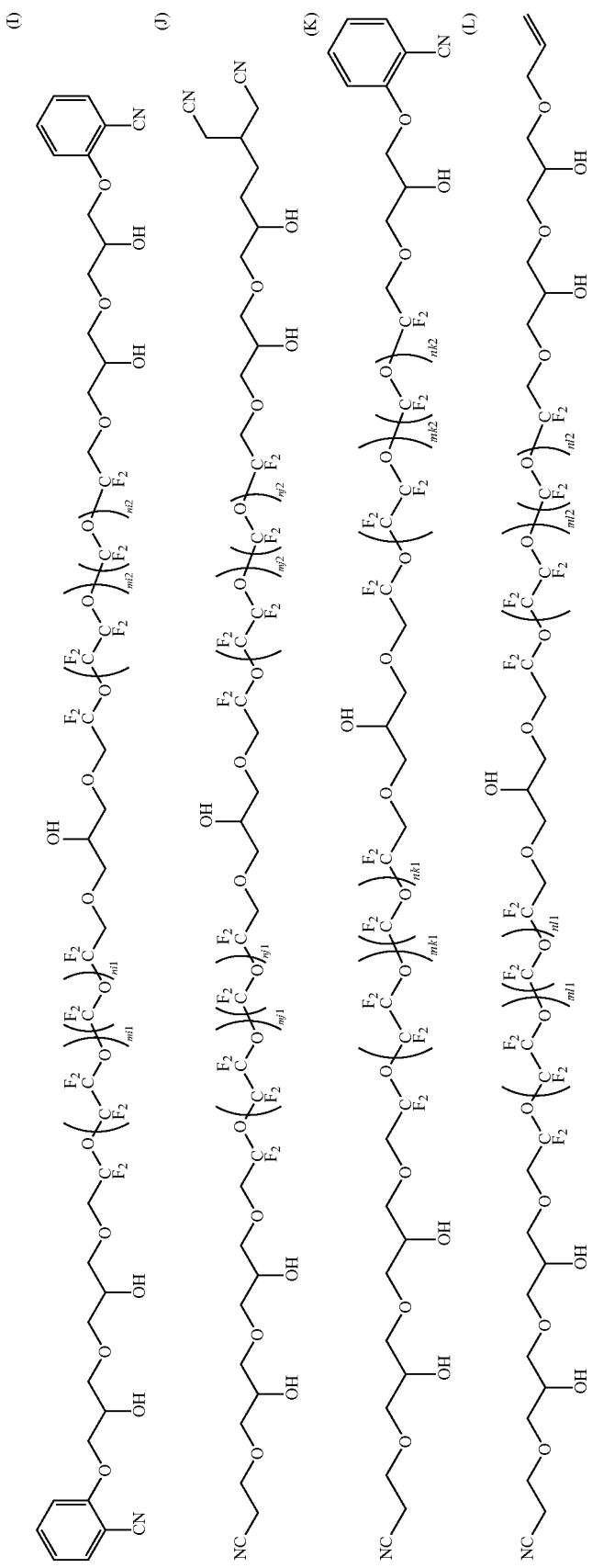

(in Formula (I), mi1, mi2, ni1, and ni2 indicate an average degree of polymerization, mi1 and mi2 represent 1 to 20, and ni1 and ni2 represent 0 to 20), (in Formula (J), mj1, mj2, nj1, and nj2 indicate an average degree of polymerization, mj1 and mj2 represent 1 to 20, and nj1 and nj2 represent 0 to 20), (in Formula (K), mk1, mk2, nk1, and nk2 indicate an average degree of polymerization, mk1 and mk2 represent 1 to 20, and nk1 and nk2 represent 0 to 20), and (in Formula (L), ml1, ml2, nl1, and nl2 indicate an average degree of polymerization, ml1 and ml2 represent 1 to 20, and nl1 and nl2 represent 0 to 20),

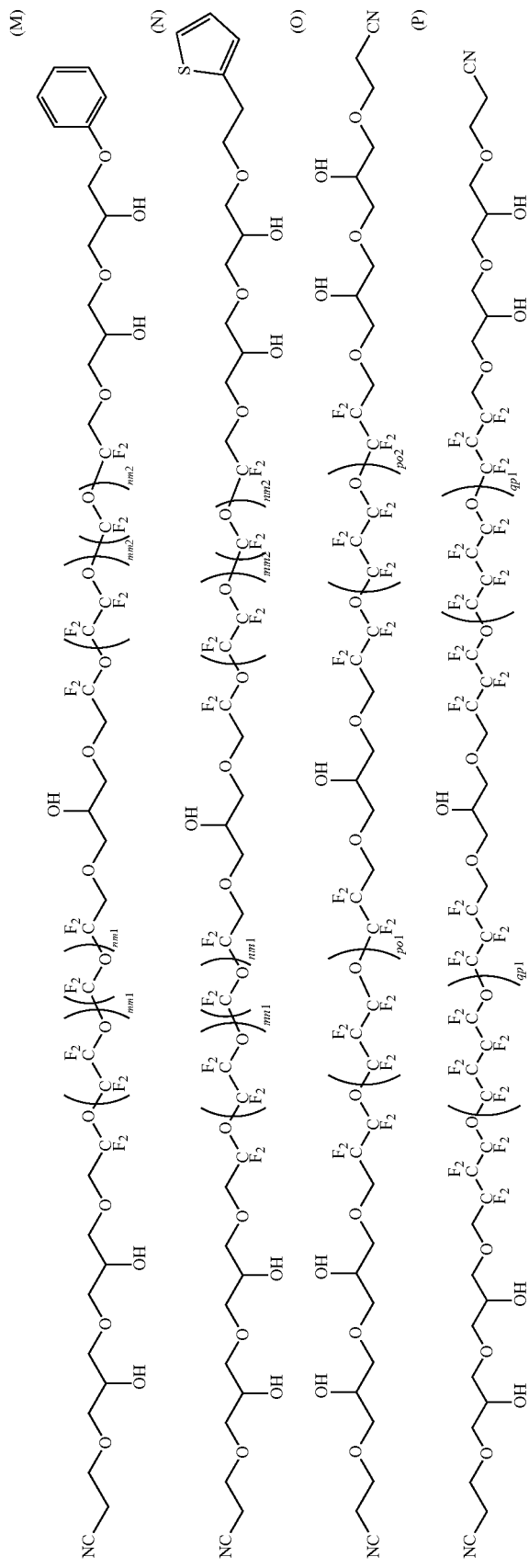

(in Formula (M), mm1, mm2, nm1, and nm2 indicate an average degree of polymerization, mm1 and mm2 represent 1 to 20, and nm1 and nm2 represent 0 to 20), (in Formula (N), mn1, mn2, nn1, and nn2 indicate an average degree of polymerization, mn1 and mn2 represent 1 to 20, and nn1 and nn2 represent 0 to 20), (in Formula (O), po1 and po2 indicate an average degree of polymerization, and each represent 1 to 20), and (in Formula (P), qp1 and qp2 indicate an average degree of polymerization, and each represent 1 to 10).

[13] The fluorine-containing ether compound according to any one of [1] to [12], wherein the number-average molecular weight thereof is in a range of 500 to 10,000.

A second aspect of the present invention is the following lubricant.

[14] A lubricant for a magnetic recording medium, which contains the fluorine-containing ether compound according to any one of [1] to [13].

A third aspect of the present invention is the following magnetic recording medium.

[15] A magnetic recording medium having at least a magnetic layer, a protective layer, and a lubricating layer sequentially provided on a substrate, wherein the lubricating layer contains the fluorine-containing ether compound according to any one of [1] to [13].

The magnetic recording medium preferably has the following feature.

[16] The magnetic recording medium according to [15], wherein the average film thickness of the lubricating layer is 0.5 nm to 2.0 nm.

Advantageous Effects of Invention

The fluorine-containing ether compound of the present invention is a compound represented by Formula (1) and is suitable as a material for a lubricant for a magnetic recording medium.

Since the lubricant for a magnetic recording medium of the present invention contains the fluorine-containing ether compound of the present invention, it is possible to form a lubricating layer having excellent adhesion and favorable chemical substance resistance and wear resistance even if the thickness is thin.

Since the magnetic recording medium of the present invention is provided with a lubricating layer having excellent adhesion and favorable chemical substance resistance and wear resistance by containing the fluorine-containing ether compound of the present invention, it has excellent reliability and durability.

BRIEF DESCRIPTION OF DRAWINGS

The FIG. is a schematic cross-sectional view showing a preferable embodiment of a magnetic recording medium of the present invention.

DESCRIPTION OF EMBODIMENTS

Hereinafter, preferable examples of a fluorine-containing ether compound, a lubricant and a magnetic recording medium of the present invention will be described in detail.

Here, the present invention is not limited only to the following embodiments. In the present invention, for example, the numbers, types, compositions, positions, amounts, ratios, materials, configurations and the like can be added, omitted, substituted or changed without departing from the scope of the present invention.

As a conventional material for a lubricant for a magnetic recording medium (hereinafter abbreviated as a "lubricant" in some cases) applied to the surface of a protective layer, a fluorine-containing ether compound having a polar group such as a hydroxyl group at a terminal of a chain structure is preferably used. The polar group in the fluorine-containing ether compound binds to an active site on the protective layer and improves the adhesiveness (adhesion) of the lubricating layer to the protective layer. For this reason, as a material of the lubricant, a fluorine-containing ether compound having a polar group not only at a terminal of a chain structure but also in the chain structure is particularly preferably used.

However, when a thin lubricating layer is formed on a protective layer using a conventional lubricant, as shown below, it is difficult to realize a lubricating layer having excellent adhesion and favorable chemical substance resistance and wear resistance.

That is, if the adhesiveness of the lubricant to the protective layer (adhesion of the lubricating layer) is insufficient, the lubricant applied onto the protective layer becomes bulky. Therefore, the coating of the lubricating layer with respect to the protective layer tends to be non-uniform. If the coating of the lubricating layer is non-uniform, the chemical substance resistance and wear resistance of the lubricating layer become insufficient. Therefore, if the adhesion of the lubricating layer is insufficient, sufficient chemical substance resistance and wear resistance cannot be obtained unless the film thickness is increased to make the coating of the lubricating layer uniform with respect to the protective layer.

Regarding a method of improving the adhesiveness of the lubricant to the protective layer (adhesion of the lubricating layer), it is conceivable to use a fluorine-containing ether compound in which polar groups are bonded to a terminal carbon atom of a chain structure, a carbon atom bonded to the terminal carbon atom, and other carbon atoms in the chain structure as a material for a lubricant.

However, in the lubricating layer formed using such a fluorine-containing ether compound, if the adhesion to the protective layer is too strong, the lubricity may be impaired, and the wear resistance may be insufficient.

The adhesion of the lubricant to the protective layer can be adjusted, for example, by changing a heat treatment temperature in a heat treatment that is performed as necessary after a lubricant containing a fluorine-containing ether compound is applied onto a protective layer. Specifically, the adhesion of the lubricant to the protective layer becomes stronger if the heat treatment temperature is raised, and becomes weaker if the heat treatment temperature is lowered.

Therefore, if the adhesion of the lubricant to the protective layer is too strong, the adhesion between the lubricating layer and the protective layer is weakened by using a method of lowering a heat treatment temperature or the like, the adhesion between the lubricating layer and the protective layer is set to have an appropriate strength, and thus the wear resistance of the lubricating layer can be improved.

However, in a lubricating layer formed using a fluorine-containing ether compound, in which polar groups are bonded to a terminal carbon atom of a chain structure thereof, to a carbon atom bonded to the terminal carbon atom thereof, and to other carbon atoms in the chain structure thereof, if the adhesion to the protective layer is weakened by using the above method or the like, the chemical substance resistance of the lubricating layer deteriorates. This is speculated to be because the proportion of polar groups that are not involved in binding to the active sites on the protective layer among polar groups in the fluorine-containing ether compound increases. That is, this is speculated to be because polar groups in the fluorine-containing ether compound that are not involved in binding to the active sites on the protective layer attract environmental substances that produce contamination substances to the lubricating layer, and the chemical substance resistance of the lubricating layer deteriorates.

Here, the inventors have focused on binding between polar groups contained in the fluorine-containing ether compound and the active sites on the protective layer, and conducted extensive studies in order to realize a fluorine-containing ether compound in which polar groups that are not involved in binding to the active sites on the protective layer are unlikely to occur and which can form a lubricating layer having uniform coating with respect to the protective layer and having favorable adhesion and favorable chemical substance resistance and wear resistance.

As a result, they found that a fluorine-containing ether compound in which a glycerin structure is disposed in the center of a chain structure, and a perfluoropolyether chain, a methylene group, a divalent linking group having a polar group, and a terminal group are bonded in that order to both sides thereof via a methylene group (—CH$_2$—), and at least one terminal group is an organic group having 1 to 8 carbon atoms and at least one of hydrogens included in the organic group is substituted by a cyano group is preferable.

In such a fluorine-containing ether compound, a carbon in the cyano group (—CN), which is included in at least one terminal group, forms sp hybrid orbital, and therefore it is difficult for the carbon to freely rotate. Therefore, the cyano group included in at least one terminal group has a smaller interaction (affinity) with the protective layer, compared with the hydroxyl group of the glycerin structure and the polar group of the divalent linking group.

Thus, in the fluorine-containing ether compound described above, the cyano group included in at least one terminal group, the hydroxyl group of the glycerin structure, and the polar group of the divalent linking group each independently can form a suitable interaction with a protective layer, and each independently bond to a plurality of functional groups (active sites) present on the protective layer. As a result, it is speculated that the fluorine-containing ether compound can form a lubricating layer having favorable adhesion to the protective layer.

In addition, in the fluorine-containing ether compound, a perfluoropolyether chain is disposed between a glycerin structure disposed in the center of the chain structure and two divalent linking groups. Therefore, the distance between the hydroxyl group (—OH) of the glycerin structure and the polar group of the divalent linking group is appropriate. Moreover, at least one terminal group is an organic group having one or more cyano groups which are less likely to rotate freely. Accordingly, binding to the active site on the protective layer with the hydroxyl group of the glycerin structure and the polar group of the divalent linking group is less likely to be inhibited by adjacent polar groups. Therefore, both the hydroxyl group of the glycerin structure and the polar group of the divalent linking group are likely to be involved in binding to the active sites on the protective layer, and are unlikely to be polar groups that are not involved in binding to the active sites on the protective layer. Therefore, in the fluorine-containing ether compound, it is possible to reduce the number of polar groups that are not involved in binding to the active sites on the protective layer, and it is possible to reduce deterioration of the chemical substance resistance and the occurrence of pickup.

In addition, in the above fluorine-containing ether compound, since the distance between the hydroxyl group of the glycerin structure and the polar group of the divalent linking group is appropriate, the hydroxyl group of the glycerin structure is less likely to aggregate with the polar group of the divalent linking group. Moreover, both terminals of each perfluoropolyether chain are brought into close contact with the protective layer by the hydroxyl group of the glycerin structure and the polar group of the divalent linking group. Therefore, the fluorine-containing ether compound applied onto the protective layer is unlikely to be bulky, the fluorine-containing ether compound easily wets and spreads on the protective layer, and a lubricating layer having uniform coating is easily obtained. Therefore, the fluorine-containing ether compound can form a lubricating layer having favorable chemical substance resistance and wear resistance.

In addition, the inventors confirmed that, when a lubricant containing the fluorine-containing ether compound is used, it is possible to form a lubricating layer having excellent adhesion even if the thickness is thin, and having favorable chemical substance resistance and wear resistance, and completed the present invention.

Hereinafter, preferable examples of a fluorine-containing ether compound, a lubricant for a magnetic recording medium and a magnetic recording medium of the present invention will be described in detail. Here, the present invention is not limited to the following embodiments.

[Fluorine-Containing Ether Compound]

The fluorine-containing ether compound of the present embodiment is represented by the following Formula (1):

$$R^1-R^2-CH_2-R^3-CH_2-OCH_2CH(OH)CH_2O-CH_2-R^3-CH_2-R^4-R^5 \quad (1)$$

(in Formula (1), $R^3$ represents a perfluoropolyether chain; $R^2$ and $R^4$ represent a divalent linking group having a polar group, and may be the same as or different from each other; $R^1$ and $R^5$ represent a terminal group bonded to an oxygen atom of $R^2$ or $R^4$, and may be the same as or different from each other; and at least one of $R^1$ and $R^5$ is an organic group having 1 to 8 carbon atoms and at least one of hydrogens included in the organic group is substituted by a cyano group).

As shown in Formula (1), the fluorine-containing ether compound of the present embodiment has a structure in which a glycerin structure is disposed in the center of the chain structure, and a perfluoropolyether chain represented by $R^3$ (hereinafter abbreviated as "PFPE chain" in some cases), a methylene group, divalent linking groups having a polar group represented by $R^2$ and $R^4$, and terminal groups represented by $R^1$ and $R^5$ are bonded in that order to both sides via a methylene group (—CH$_2$—). In Formula (1), at least one terminal group of $R^1$ and $R^5$ is an organic group having 1 to 8 carbon atoms, and at least one of hydrogens included in the organic group is substituted by a cyano group (hereinafter described as "organic group substituted with a cyano group" in some cases).

(Glycerin Structure)

In the fluorine-containing ether compound represented by Formula (1), the hydroxyl group (—OH) of the glycerin structure (—OCH$_2$CH(OH)CH$_2$O—) disposed in the center of the chain structure adheres the fluorine-containing ether compound and the protective layer to form a thin lubricating layer with sufficient coverage.

In addition, oxygen atoms disposed at both terminals of the glycerin structure form an ether bond (—O—) with methylene groups (—CH$_2$—) disposed on both sides. These two ether bonds impart appropriate flexibility to the fluorine-containing ether compound represented by Formula (1), and increase the affinity between the hydroxyl group of the glycerin structure and the protective layer.

(PFPE Chain Represented by R$^3$)

In the fluorine-containing ether compound represented by Formula (1), when the lubricant containing the fluorine-containing ether compound of the present embodiment is applied onto the protective layer to form a lubricating layer, the PFPE chain represented by R$^3$ covers the surface of the protective layer, imparts lubricity to the lubricating layer, and reduces the frictional force between the magnetic head and the protective layer. The PFPE chain is appropriately selected depending on the performance and the like required for the lubricant containing a fluorine-containing ether compound.

Examples of PFPE chains include those composed of perfluoroalkylene oxide polymers or copolymers. Examples of perfluoroalkylene oxides include perfluoromethylene oxide, perfluoroethylene oxide, perfluoro-n-propylene oxide, and perfluorobutylene oxide.

Specifically, in Formula (1), R$^3$ is preferably any one selected from the group consisting of PFPE chains represented by the following Formulae (3) to (5). When R$^3$ is any one selected from the group consisting of PFPE chains represented by Formulae (3) to (5), a fluorine-containing ether compound which can form a lubricating layer having favorable lubricity is obtained. When R$^3$ is any one selected from the group consisting of PFPE chains represented by Formulae (3) to (5), the ratio of the number of oxygen atoms (the number of ether bonds (—O—)) to the number of carbon atoms in the PFPE chain is appropriate. Therefore, the fluorine-containing ether compound having an appropriate hardness is obtained. Therefore, the fluorine-containing ether compound applied onto the protective layer is less likely to aggregate on the protective layer, and an even thinner lubricating layer can be formed with sufficient coverage. In Formula (1), R$^3$ is particularly preferably a PFPE chain represented by Formula (3) so that the fluorine-containing ether compound has appropriate flexibility and thus can form a lubricating layer having better chemical substance resistance and wear resistance.

CF$_2$—(OCF$_2$CF$_2$)$_b$—(OCF$_2$)$_c$—OCF$_2$—     (3)

(in Formula (3), b and c indicate an average degree of polymerization, b represents 1 to 20, and c represents 0 to 20),

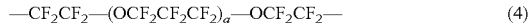

—CF$_2$CF$_2$—(OCF$_2$CF$_2$CF$_2$)$_d$—OCF$_2$CF$_2$—     (4)

(in Formula (4), d indicates an average degree of polymerization, and represents 1 to 20), and

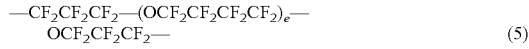

—CF$_2$CF$_2$CF$_2$—(OCF$_2$CF$_2$CF$_2$CF$_2$)$_e$— OCF$_2$CF$_2$CF$_2$—     (5)

(in Formula (5), e indicates an average degree of polymerization, and represents 1 to 10).

In Formula (3), the arrangement sequence of the repeating units (OCF$_2$CF$_2$) and (OCF$_2$) is not particularly limited. In Formula (3), the number b of (OCF$_2$CF$_2$) and the number c of (OCF$_2$) may be the same as or different from each other. The PFPE chain represented by Formula (3) may be a polymer of (OCF$_2$CF$_2$). In addition, the PFPE chain represented by Formula (3) may be any one of a random copolymer, a block copolymer, and an alternating copolymer composed of (OCF$_2$CF$_2$) and (OCF$_2$).

In Formulae (4) and (5), since d which indicates an average degree of polymerization is 1 to 20, e is 1 to 10 (or in Formula (3), b is 1 to 20, and c is 0 to 20), a fluorine-containing ether compound which can form a lubricating layer having favorable lubricity is obtained. In addition, in Formulae (3) to (5), since b, c, and d which indicate average degrees of polymerization are 20 or less, and e is 10 or less, the viscosity of the fluorine-containing ether compound does not become too high, and a lubricant containing the compound is preferable because it is easy to apply. b, c, d, and e which indicate average degrees of polymerization are preferably 2 to 10 and more preferably 3 to 7 so that the fluorine-containing ether compound becomes a compound which easily wets and spreads on the protective layer and allows a lubricating layer having a uniform film thickness to be easily obtained.

In the fluorine-containing ether compound represented by Formula (1), two PFPE chains represented by R$^3$ may be the same as or different from each other.

(Divalent Linking Groups Having a Polar Group Represented by R$^2$ and R$^4$)

In the fluorine-containing ether compound represented by Formula (1), R$^2$ and R$^4$ represent a divalent linking group having a polar group. In the fluorine-containing ether compound represented by Formula (1), since R$^2$ and R$^4$ have a polar group, when a lubricant containing the compound is used to form a lubricating layer on the protective layer, a suitable interaction occurs between the lubricating layer and the protective layer. The divalent linking group having a polar group constituting R$^2$ and R$^4$ can be appropriately selected depending on the performance and the like required for the lubricant containing a fluorine-containing ether compound.

Examples of polar groups of divalent linking groups having a polar group represented by R$^2$ and R$^4$ include a hydroxyl group (—OH), an amino group (—NH$_2$), a carboxyl group (—COOH), an aldehyde group (—COH), a carbonyl group (—CO—), and a sulfonic acid group (—SO$_3$H). Among these, particularly, the polar group is preferably a hydroxyl group. The hydroxyl group has a large interaction with the protective layer, particularly the protective layer formed of a carbon-based material. Therefore, when the polar group of R$^2$ and/or R$^4$ is a hydroxyl group, the lubricating layer containing the fluorine-containing ether compound has high adhesiveness (adhesion) to the protective layer.

When the polar group of R$^2$ and/or R$^4$ contains a hydroxyl group, the total number of a hydroxyl group contained in R$^2$ and a hydroxyl group contained in R$^4$ in Formula (1) is preferably 2 to 6, more preferably 2 to 5, and still more preferably 3 to 4. When the total number of the hydroxyl groups is 2 or more, the interaction between the hydroxyl groups of R$^2$ and R$^4$ and the protective layer can be obtained more effectively. As a result, a fluorine-containing ether compound which can form a lubricating layer having a higher adhesiveness (adhesion) to the protective layer is obtained. In addition, when the total number of the hydroxyl groups is 6 or less, it is possible to reduce the occurrence of pickup, because it is possible to prevent polar groups which are not involved in bonding between the lubricating layer and the active sites on the protective layer from attracting environmental substances, which produce contamination substances, to the lubricating layer.

It is preferable for R$^2$ and/or R$^4$ to contain 1 to 3 linking groups represented by the following Formula (2), and it is more preferable that both $R^2$ and $R^4$ contain 1 to 3 linking groups represented by the following Formula (2):

$$—CH_2CH(OH)CH_2— \quad (2)$$

The linking group represented by Formula (2) is a linking group having a hydroxyl group, which is a group having a particularly large interaction with the protective layer among polar groups. In addition, in the linking group represented by Formula (2), a methylene group (—$CH_2$—) is disposed on both sides of the carbon atom to which the hydroxyl group is bonded. Therefore, when $R^2$ and/or $R^4$ contains 1 to 3 linking groups represented by Formula (2), for the following reasons, a fluorine-containing ether compound which can form a lubricating layer with higher adhesiveness (adhesion) to the protective layer is obtained.

That is, at least the methylene group and the oxygen atom (—O—) of $R^2$ or $R^4$ are disposed between the carbon atom to which the hydroxyl group of the linking group represented by Formula (2) is bonded and $R^1$ or $R^5$. Therefore, the distance between the hydroxyl group contained in the linking group represented by Formula (2) and the cyano group included in $R^1$ and/or $R^5$ is appropriate. Therefore, the hydroxyl group of the linking group represented by Formula (2) and the terminal group represented by $R^1$ and/or $R^5$ each independently exhibit a favorable interaction with the protective layer, and each is independently likely to be bonded to a plurality of functional groups (active sites) present on the protective layer.

In addition, in the linking group represented by Formula (2), since a methylene group is disposed on both sides of the carbon atom to which the hydroxyl group is bonded, when $R^2$ and/or $R^4$ contains 2 to 3 linking groups represented by Formula (2), the distance between the hydroxyl groups contained in the linking groups represented by Formula (2) is appropriate. As a result, even if the number of hydroxyl groups contained in the linking groups represented by Formula (2) is plural, the hydroxyl groups contained in the linking groups represented by Formula (2) are likely to be involved in binding to the active sites on the protective layer.

In addition, when $R^2$ and/or $R^4$ contains 1 to 3 linking groups represented by Formula (2), $R^2$ and/or $R^4$ contains 1 to 3 hydroxyl groups. Therefore, the number of hydroxyl groups contained in $R^2$ and/or $R^4$ tends to be appropriate, and it is possible to prevent the polarity of the fluorine-containing ether compound from becoming too high and to prevent pickup from occurring.

The number of linking groups represented by Formula (2) is preferably adjusted so that the total number of a hydroxyl group contained in $R^2$ and a hydroxyl group contained in $R^4$ in Formula (1) becomes 2 to 5, and is more preferably adjusted so that the total number becomes 3 to 4, since a fluorine-containing ether compound which can form a lubricating layer with better adhesion to the protective layer is obtained.

$R^2$ and/or $R^4$ is preferably a linking group represented by the following Formula (2-1), and more preferably, both $R^2$ and $R^4$ are linking groups represented by the following Formula (2-1). In Formula (2-1), the oxygen atom on the left side is an oxygen atom bonded to $R^1$ or $R^5$.

$$—O—X—(Y^1X)_a—Y^2— \quad (2\text{-}1)$$

(in Formula (2-1), a represents an integer of 0 to 2; X represents Formula (2); $Y^1$ represents any one selected from the group consisting of —O—, —$CH_2$—, —$CH_2O$—, and —$OCH_2$—; and $Y^2$ represents —O— or —$CH_2O$—).

$R^2$ and/or $R^4$ is preferably a linking group represented by Formula (2-1) so that the fluorine-containing ether compound is easily synthesized.

In the linking group represented by Formula (2-1), in Formula (2-1), a represents an integer of 0 to 2. Since a in the linking group represented by Formula (2-1) is 0 or more, when $R^2$ and/or $R^4$ is a linking group represented by Formula (2-1), 1 or more hydroxyl groups, which have a particularly large interaction with the protective layer, are contained as polar groups. As a result, a fluorine-containing ether compound which can form a lubricating layer with better adhesion to the protective layer is obtained. In addition, in the linking group represented by Formula (2-1), since a in Formula (2-1) is 2 or less, it is possible to prevent the occurrence of pickup, in which the polarity of the fluorine-containing ether compound becomes too high due to a large number of hydroxyl groups in the linking group represented by Formula (2-1), and the lubricant containing the compound adheres as foreign matter (smear).

In addition, in the linking group represented by Formula (2-1), when a in Formula (2-1) is 1 or 2, the distance between the hydroxyl groups contained in the linking group represented by Formula (2-1) is appropriate. As a result, even if the number of hydroxyl groups contained in $R^2$ and/or $R^4$ is plural, the hydroxyl groups contained in $R^2$ and/or $R^4$ are likely to be involved in binding to the active sites on the protective layer.

In the linking group represented by Formula (2-1), X in Formula (2-1) is Formula (2), $Y^1$ represents any one selected from the group consisting of —O—, —$CH_2$—, —$CH_2O$—, and —$OCH_2$—, and $Y^2$ represents —O— or —$CH_2O$—. $Y^1$ and $Y^2$ may be the same as or different from each other.

When $R^2$ and/or $R^4$ is a linking group represented by Formula (2-1), $R^2$ and $R^1$, and/or $R^4$ and $R^5$ are bonded by an ether bond, and an ether bond is provided between $R^2$ and $R^3$ and/or between $R^4$ and $R^3$. As a result, a fluorine-containing ether compound having appropriate flexibility is obtained, and a lubricating layer having better chemical substance resistance and wear resistance can be formed.

In the linking group represented by Formula (2-1), $Y^1$ is preferably an ether bond (—O—) or a group containing an ether bond, and more preferably, $Y^1$ and $Y^2$ are —O—. In this case, compared with when $Y^1$ is $CH_2$, a fluorine-containing ether compound having appropriate flexibility is obtained. Therefore, the interaction between the hydroxyl group contained in the linking group represented by Formula (2-1) and the protective layer becomes strong.

In the fluorine-containing ether compound represented by Formula (1), $R^2$ and $R^4$ may be the same as or different from each other.

(Terminal Groups Represented by $R^1$ and $R^5$)

In the fluorine-containing ether compound represented by Formula (1), at least one of the terminal groups represented by $R^1$ and $R^5$ is an organic group having 1 to 8 carbon atoms wherein at least one of hydrogens included in the organic group is substituted by a cyano group (—CN) (organic group substituted with a cyano group).

In the fluorine-containing ether compound represented by Formula (1), the cyano group included in the organic group substituted with a cyano group exhibits a favorable interaction with the protective layer. Therefore, the organic group substituted with a cyano group has a function of improving the adhesion between the lubricating layer and the protective layer and forming a lubricating layer having favorable chemical substance resistance and wear resistance.

In the fluorine-containing ether compound represented by Formula (1), the type of the organic group substituted with a cyano group can be appropriately selected depending on the performance and the like required for the lubricant containing a fluorine-containing ether compound.

The number of cyano groups included in the organic group substituted with a cyano group is not particularly limited, and it may be one, or two or more. The number of cyano groups included in the organic group substituted with a cyano group is preferably one, since such a fluorine-containing ether compound is relatively easily produced.

The organic group in the organic group substituted with a cyano group has 1 to 8 carbon atoms. In the fluorine-containing ether compound represented by Formula (1), since the number of the carbon atoms is 1 to 8, the organic group substituted with the cyano group does not cause steric hindrance and a fluorine-containing ether compound is obtained wherein favorable affinity between the protective layer and the cyano group is obtained.

The organic group in the organic group substituted with a cyano group is preferably a phenyl group, or an alkyl group having 1 to 8 carbon atoms, and more preferably a phenyl group, or an alkyl group having 1 to 5 carbon atoms. When the organic group in the organic group substituted with a cyano group is a phenyl group, or an alkyl group having 1 to 5 carbon atoms, steric hindrance of the organic group of the organic group substituted with a cyano group is more effectively suppressed, and a fluorine-containing ether compound is obtained wherein affinity between the protective layer and the cyano group is large.

Specifically, as the organic group substituted with a cyano group, examples include any of organic groups represented by the following Formulae (6-1) to (6-4) and (7) to (11).

The dotted line shown in Formulae (6-1) to (6-4) and (7) to (11) represents a bond bonded to $R^2$ or $R^4$ in Formula (1).

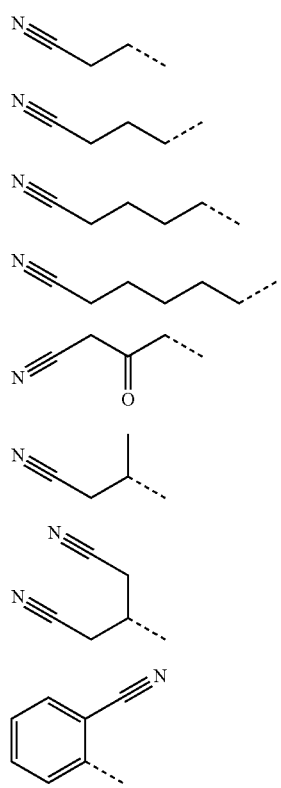

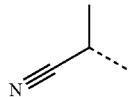

Among the organic groups substituted with a cyano group represented by Formulae (6-1) to (6-4) and (7) to (11), it is preferable to use any one selected from the organic group represented by Formula (6-1) and the organic groups represented by Formulae (7) to (10) to provide a fluorine-containing ether compound which can form favorable affinity with the protective layer of the magnetic recording medium, it is more preferable to use the organic group represented by Formula (6-1) or the organic group represented by Formula (10) to provide a fluorine-containing ether compound which is relatively easily produced, and it is most preferable to use the organic group represented by Formula (6-1).

In the fluorine-containing ether compound represented by Formula (1), when both terminal groups represented by $R^1$ and $R^5$ are the organic group substituted with a cyano group, $R^1$ and $R^5$ may be the same as or different from each other.

In the fluorine-containing ether compound represented by Formula (1), when only one (for example, $R^5$) of the terminal groups represented by $R^1$ and $R^5$ is the organic group substituted with a cyano group, the other terminal group (for example, $R^1$) which is not the organic group substituted with a cyano group may be any group, and is not particularly limited. When only one of the terminal groups represented by $R^1$ and $R^5$ is the organic group substituted with a cyano group, the other terminal group is preferably an organic group which includes at least one double bond or triple bond, and examples thereof include an aromatic hydrocarbon-containing group, an aromatic heterocycle-containing group, a group containing an alkenyl group and a group containing an alkynyl group. The other terminal group may include a hydroxyl group, but preferably does not include a hydroxyl group in order to prevent the wear resistance of the lubricating layer from being impaired due to an excessive number of hydroxyl groups.

Specifically, as the other terminal group, any group selected from the group consisting of a phenyl group, a methoxyphenyl group, a phenylfluoride group, a naphthyl group, a phenethyl group, a methoxyphenethyl group, a phenethylfluoride group, a benzyl group, a methoxybenzyl group, a naphthylmethyl group, a methoxynaphthyl group, a pyrrolyl group, a pyrazolyl group, a methylpyrazolylmethyl group, an imidazolyl group, a furyl group, a furfuryl group, an oxazolyl group, an isooxazolyl group, a thienyl group, a thienylethyl group, a thiazolyl group, a m ethylthiazolylethyl group, an isothiazolyl group, a pyridyl group, a pyrimidinyl group, a pyridazinyl group, a pyrazinyl group, an indolinyl group, a benzofuranyl group, a benzothienyl group, a benzoimidazolyl group, a benzooxazolyl group, a benzothiazolyl group, a benzopyrazolyl group, a benzoisooxazolyl group, a benzoisothiazolyl group, a quinolyl group, an isoquinolyl group, a quinazolinyl group, a quinoxalinyl group, a phthalazinyl group, a cinnolinyl group, a vinyl group, an allyl group, a butenyl group, a propynyl group, a propargyl group, a butynyl group, a methylbutynyl group, a pentynyl group, a methylpentynyl group and a hexynyl group can be used.

Among these, any group selected from the group consisting of a phenyl group, a methoxyphenyl group, a thienylethyl group, a butenyl group, an allyl group, a propargyl group, a phenethyl group, a methoxyphenethyl group, and a phenethylfluoride group is particularly preferable as the other terminal group. In this case, such a fluorine-containing ether compound is provided which can form a lubricating layer having more excellent chemical substance resistance and wear resistance.

The other terminal group may have a substituent such as an alkyl group, an alkoxy group, a hydroxyl group, a thiol group, a carboxyl group, a carbonyl group, and an amino group.

In the fluorine-containing ether compound represented by Formula (1), when only one of the terminal groups represented by $R^1$ and $R^5$ is the organic group substituted with a cyano group, it is preferable that one of $R^1$ and $R^5$ is a phenyl group which is substituted with at least one cyano group, or an alkyl group having 1 to 5 carbon atoms which is substituted with at least one cyano group, and the other is an organic group which includes at least one selected from the group consisting of an aromatic hydrocarbon-containing group, an aromatic heterocycle-containing group, an alkenyl group, and an alkynyl group. In this case, such a fluorine-containing ether compound is provided which can form a lubricating layer having a favorable chemical substance resistance and wear resistance.

In the fluorine-containing ether compound represented by Formula (1), when two PFPE chains represented by $R^3$ are the same, $R^2$ and $R^4$ are the same, and $R^1$ and $R^5$ are the same, this is preferable because the compound can be easily and efficiently produced. In addition, since such a fluorine-containing ether compound has a symmetric structure with a glycerin structure as the center, this is preferable because the compound is likely to uniformly wet and spread on the protective layer, and a lubricating layer having uniform thickness is easily obtained.

Specifically, the fluorine-containing ether compound represented by Formula (1) is preferably any of the compounds represented by the following Formulae (A) to (P). Here, in Formulae (A) to (P), since ma1 to mn1, ma2 to mn2, na1 to nn1, na2 to nn2, po1, po2, qp1, and qp2 are values indicating an average degree of polymerization, they are not necessarily integers.

When the compound represented by Formula (1) is any of the compounds represented by Formulae (A) to (P), this is preferable because a raw material is easily available, and moreover, it is possible to form a lubricating layer having excellent adhesion and better chemical substance resistance and wear resistance even if the thickness is thin.

In all of the compounds represented by the following Formulae (A) to (P), two PFPE chains represented by $R^3$ in Formula (1) are the same. In all of the compounds represented by the following Formulae (A) to (P), $R^2$ and $R^4$ are a linking group represented by Formula (2-1), and $Y^2$ in Formula (2-1) is —O—.

In all of the compounds represented by the following Formulae (A) to (E), both $R^1$ and $R^5$ are organic groups represent by Formula (6-1), and $R^2$ and $R^4$ are linking groups represented by Formula (2-1) and $R^3$ is represented by Formula (3).

In all of the compounds represented by Formulae (A) to (C), a in Formula (2-1) for $R^2$ is 0. In the compound represented by Formula (A), a in Formula (2-1) for $R^4$ is 0, in the compound represented by Formula (B), a in Formula (2-1) for $R^4$ is 1, and $Y^1$ represents —O—, and in the compound represented by Formula (C), a in Formula (2-1) for $R^4$ is 2, and $Y^1$ represents —O—.

In the compounds represented by Formulae (D) and (E), a in Formula (2-1) for $R^2$ is 1, and $Y^1$ represents —O—. In the compound represented by Formula (D), a in Formula (2-1) for $R^4$ is 1, and $Y^1$ represents —O—. In the compound represented by Formula (E), a in Formula (2-1) for $R^4$ is 2, and $Y_1$ represents —O—.

In the compounds represented by the following Formulae (F), (G) and (I), $R^2$ and $R^4$ are linking groups represented by Formula (2-1), a in Formula (2-1) is 1, $Y^1$ represents —O—, and $R^3$ is represented by Formula (3).

In the compound represented by Formula (F), $R^1$ and $R^5$ represent the Formula (8), in the compound represented by Formula (G), $R^1$ and $R^5$ represent the Formula (9), and in the compound represented by Formula (I), $R^1$ and $R^5$ represent the Formula (10).

In the compound represented by the following Formula (H), $R^1$ and $R^5$ represent Formula (7), $R^2$ and $R^4$ are linking groups represented by Formula (2-1), a in Formula (2-1) is 0, and $R^3$ is represented by Formula (3).

In the compounds represented by the following Formulae (J) to (N), $R^1$ is an organic group represented by Formula (6-1), $R^2$ and $R^4$ are linking groups represented by Formula (2-1), and $R^3$ is represented by Formula (3).

In the compounds represented by Formulae (J), (L) to (N), a in Formula (2-1) for $R^2$ and $R^4$ is 1, and $Y^1$ represents —O—. In the compound represented by Formula (K), a in Formula (2-1) for $R^2$ is 1, and $Y^1$ represents —O— and a in Formula (2-1) for $R^4$ is 0.

In the compound represented by Formula (J), $R^5$ represents Formula (9), in the compound represented by Formula (K), $R^5$ represents Formula (10), in the compound represented by Formula (L), $R^5$ represents an allyl group, in the compound represented by Formula (M), $R^5$ represents a phenyl group, and in the compound represented by Formula (N), $R^5$ represents a thienylethyl group.

In the compounds represented by the following Formulae (O) and (P), both $R^1$ and $R^5$ are an organic group represented by Formula (6-1), $R^2$ and $R^4$ are a linking group represented by Formula (2-1), a in Formula (2-1) is 1, and $Y^1$ represents —O—. In the compound represented by Formula (0), $R^3$ is represented by Formula (4). In the compound represented by Formula (P), $R^3$ is represented by Formula (5).

(A)

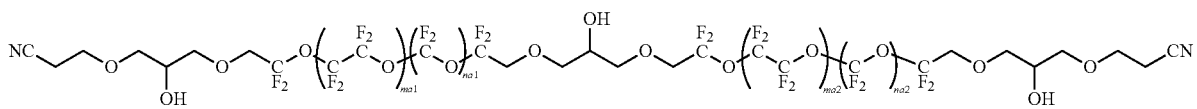

(B)
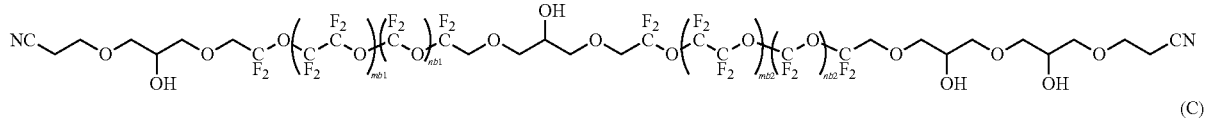

(C)
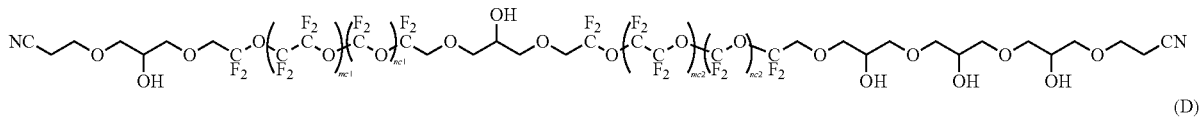

(D)
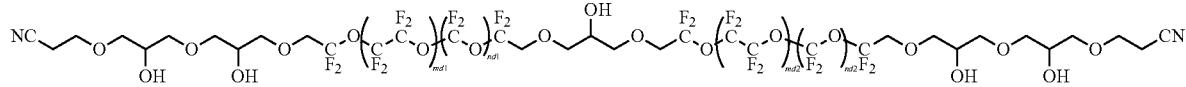

(in Formula (A), ma1, ma2, na1, and na2 indicate an average degree of polymerization, ma1 and ma2 represent 1 to 20, and na1 and na2 represent 0 to 20), (in Formula (B), mb1, mb2, nb1, and nb2 indicate an average degree of polymerization, mb1 and mb2 represent 1 to 20, and nb1 and nb2 represent 0 to 20), (in Formula (C), mc1, mc2, nc1, and nc2 indicate an average degree of polymerization, mc1 and mc2 represent 1 to 20, and nc1 and nc2 represent 0 to 20), (in Formula (D), md1, md2, nd1, and nd2 indicate an average degree of polymerization, md1 and md2 represent 1 to 20, and nd1 and nd2 represent 0 to 20).

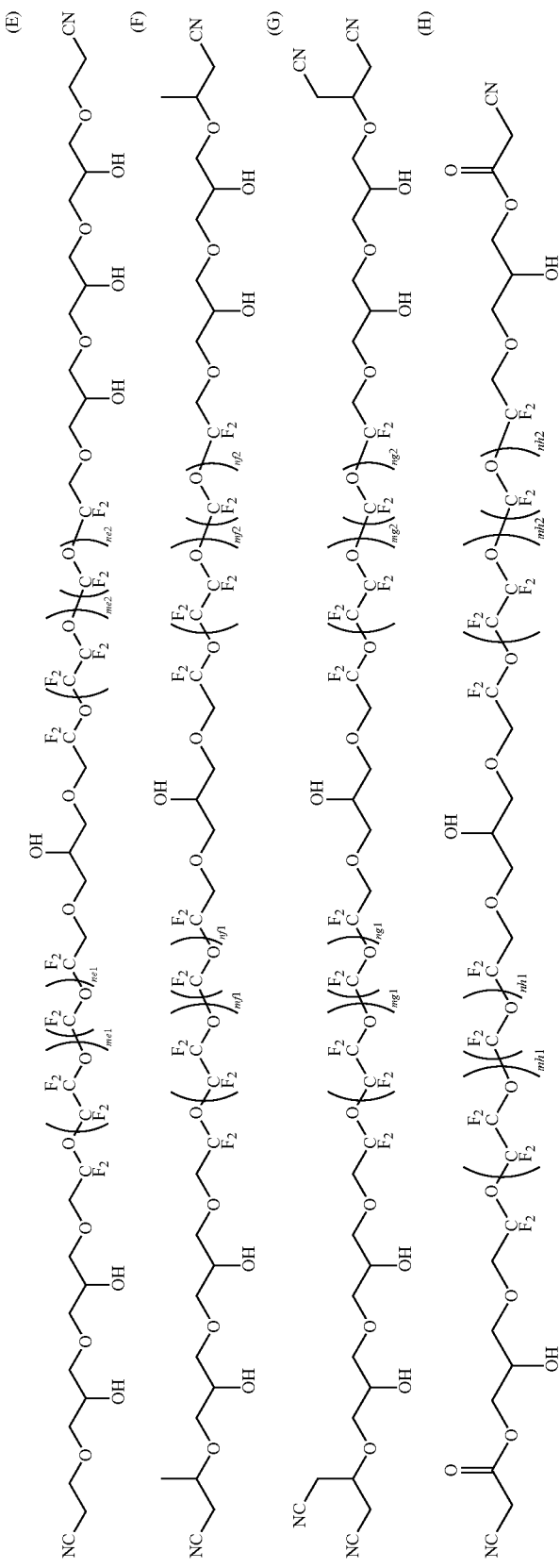

(in Formula (E), me1, me2, ne1, and ne2 indicate an average degree of polymerization, me1 and me2 represent 1 to 20, and ne1 and ne2 represent 0 to 20), (in Formula (F), mf1, mf2, nf1, and nf2 indicate an average degree of polymerization, mf1 and mf2 represent 1 to 20, and nf1 and nf2 represent 0 to 20), (in Formula (G), mg1, mg2, ng1, and ng2 indicate an average degree of polymerization, mg1 and mg2 represent 1 to 20, and ng1 and ng2 represent 0 to 20), and (in Formula (H), mh1, mh2, nh1, and nh2 indicate an average degree of polymerization, mh1 and mh2 represent 1 to 20, and nh1 and nh2 represent 0 to 20).

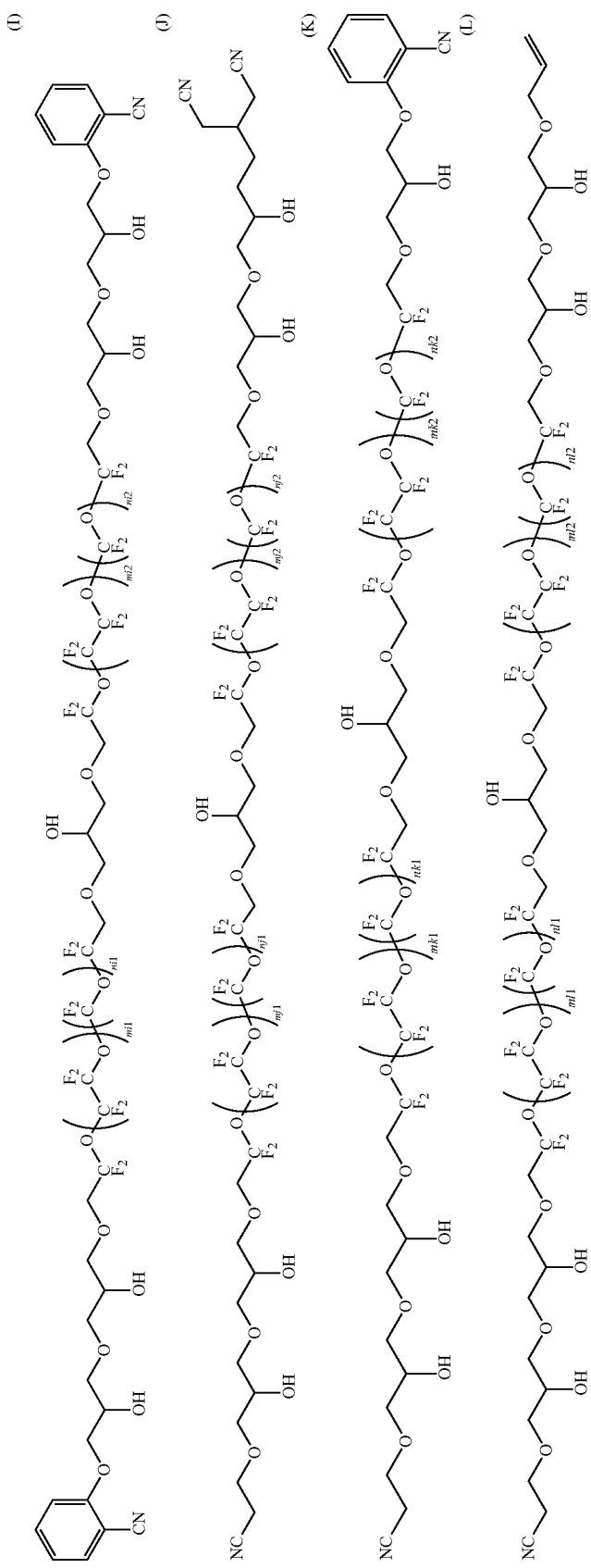

(in Formula (I), mi1, mi2, ni1, and ni2 indicate an average degree of polymerization, mi1 and mi2 represent 1 to 20, and ni1 and ni2 represent 0 to 20), (in Formula (J), mj1, mj2, nj1, and nj2 indicate an average degree of polymerization, mj1 and mj2 represent 1 to 20, and nj1 and nj2 represent 0 to 20), (in Formula (K), mk1, mk2, nk1, and nk2 indicate an average degree of polymerization, mk1 and mk2 represent 1 to 20, and nk1 and nk2 represent 0 to 20), and (in Formula (L), ml1, ml2, nl1, and nl2 indicate an average degree of polymerization, ml1 and ml2 represent 1 to 20, and nl1 and nl2 represent 0 to 20).

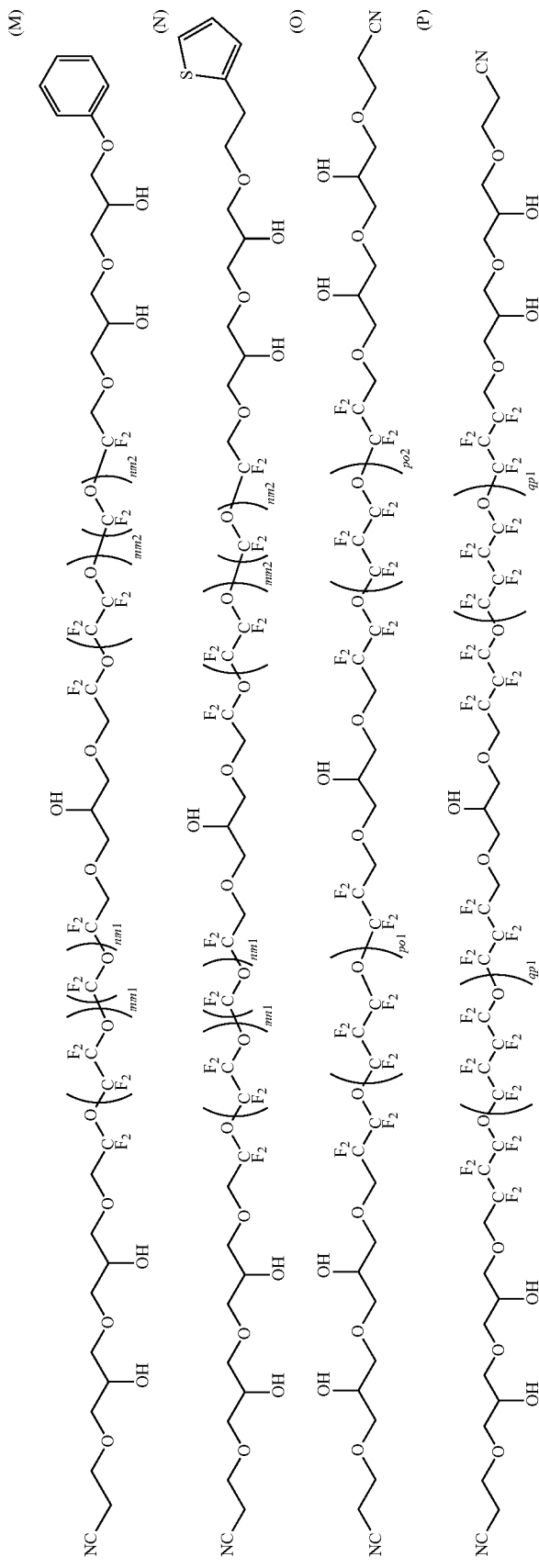

(in Formula (M), mm1, mm2, nm1, and nm2 indicate an average degree of polymerization, mm1 and mm2 represent 1 to 20, and nm1 and nm2 represent 0 to 20), (in Formula (N), mn1, mn2, nn1, and nn2 indicate an average degree of polymerization, mn1 and mn2 represent 1 to 20, and nn1 and nn2 represent 0 to 20), (in Formula (O), po1 and po2 indicate an average degree of polymerization, and each represent 1 to 20), and (in Formula (P), qp1 and qp2 indicate an average degree of polymerization, and each represent 1 to 10).

In Formulae (A) to (P), ma1 to mn1, ma2 to mn2, na1 to nn1, na2 to nn2, po1, po2, qp1, and qp2 may each have a range arbitrarily selected from the ranges described above. For example, ma1 to mn1, ma2 to mn2, po1, and po2 may be 1 to 15, 1 to 10, 1 to 8, 1 to 5, 2 to 3, or the like. na1 to nn1, and na2 to nn2 may be 0 to 15, 0 to 10, 0 to 8, 0 to 5, 1 to 6, 2 to 3, or the like. qp1 and qp2 may be 1 to 8, 1 to 5, 2 to 3, or the like.

The number-average molecular weight (Mn) of the fluorine-containing ether compound of the present embodiment is preferably in a range of 500 to 10,000, and particularly preferably in a range of 1,000 to 5,000. If the number-average molecular weight is 500 or more, the lubricating layer composed of the lubricant containing the fluorine-containing ether compound of the present embodiment has excellent heat resistance. The number-average molecular weight of the fluorine-containing ether compound is more preferably 1,000 or more. In addition, when the number-average molecular weight is 10,000 or less, the viscosity of the fluorine-containing ether compound becomes appropriate, and when a lubricant containing the compound is applied, a lubricating layer having a thin film thickness can be easily formed. The number-average molecular weight of the fluorine-containing ether compound is preferably 5,000 or less so that the compound has a viscosity at which handling is easy when applied to a lubricant.

The number-average molecular weight (Mn) of the fluorine-containing ether compound are values measured by $^1$H-NMR and $^{19}$F-NMR, specifically, by $^1$H-NMR and $^{19}$F-NMR using AVANCEIII400 (commercially available from Bruker BioSpin). More specifically, the number of repeating units of the PFPE chain is calculated from the integrated value measured by $^{19}$F-NMR to obtain a number-average molecular weight. In the measurement of nuclear magnetic resonance (NMR), a sample is diluted with a hexafluorobenzene/d-acetone (4/1 v/v) solvent, and measurement is performed. The standard for $^{19}$F-NMR chemical shift is −164.7 ppm for the peak of hexafluorobenzene, and the standard for $^1$H-NMR chemical shift is 2.2 ppm for the peak of acetone.

The fluorine-containing ether compound of the present embodiment preferably has a molecular weight dispersity (ratio of weight-average molecular weight (Mw)/number-average molecular weight (Mn)) of 1.3 or less, by performing molecular weight fractionation by an appropriate method.

In the present embodiment, the method for molecular weight fractionation is not particularly limited, and for example, molecular weight fractionation using a silica gel column chromatography method, a gel permeation chromatography (GPC) method or the like, molecular weight fractionation using a supercritical extraction method, or the like can be used.

"Production Method"

A method of producing a fluorine-containing ether compound of the present embodiment is not particularly limited, and a conventionally known production method can be used for production. The fluorine-containing ether compound of the present embodiment can be produced using, for example, the following production method.

(When Two PFPE Chains Represented by $R^3$ are the Same, and $R^1$—$R^2$— and $R^5$—$R^4$— are the Same)

When a compound in which, in Formula (1) two PFPE chains represented by $R^3$ are the same, and $R^1$—$R^2$— and $R^5$—$R^4$— are the same (that is, $R^1$ and $R^5$ are the same and $R^2$ and $R^4$ are the same) is produced, first, a fluorine-based compound in which a hydroxymethyl group (—CH$_2$OH) is disposed at both terminals of the perfluoropolyether chain corresponding to $R^3$ in Formula (1) is prepared.

Next, the hydroxyl group of the hydroxymethyl group disposed at one terminal of the fluorine-based compound and the epoxy group of an epoxy compound having a group that forms $R^1$—$R^2$— (=group that forms $R^5$—$R^4$—) in Formula (1) are reacted. Accordingly, an intermediate compound having a group corresponding to $R^1$—$R^2$— at one terminal of the perfluoropolyether chain corresponding to $R^3$ is obtained.

Regarding the epoxy compound having a group that forms $R^1$—$R^2$— (=group that forms $R^5$—$R^4$—) in Formula (1), for example, the compounds represented by the following Formulae (6a) to (11a), (6b) to (11b) and (6c) can be used.

When the fluorine-based compound is reacted with the epoxy compound to synthesize the intermediate compound, the hydroxyl group of the epoxy compound may be protected using an appropriate protecting group, and then reacted with the fluorine-based compound.

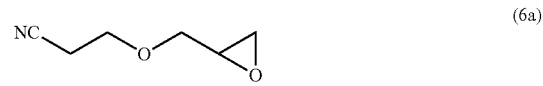

(6a)

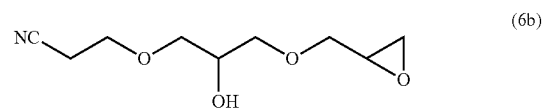

(6b)

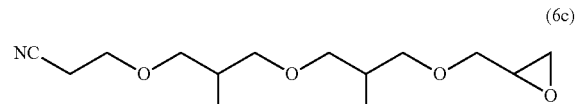

(6c)

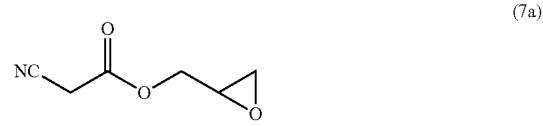

(7a)

(7b)

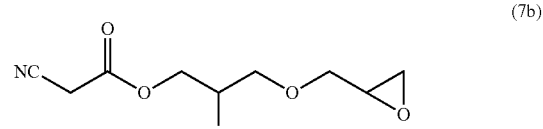

(8a)

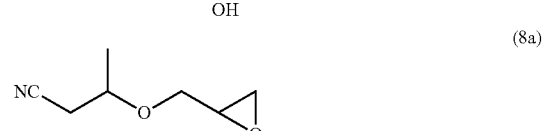

(8b)

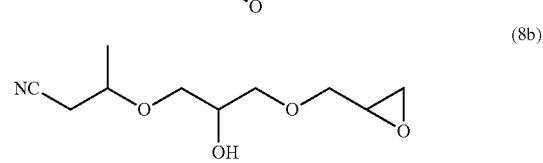

-continued

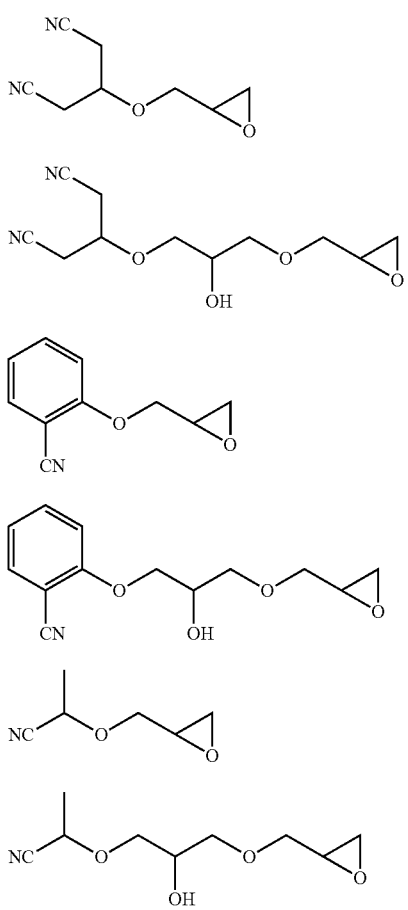

(9a)
(9b)
(10a)
(10b)
(11a)
(11b)

The epoxy compound having a group that forms $R^1$—$R^2$— (=group that forms $R^5$—$R^4$—) in Formula (1) can be produced, for example, as shown in the following Formula (12), using a method of reacting an alcohol having a structure corresponding to the terminal group represented by $R^1$ or $R^5$ in Formula (1) with epibromohydrin.

In addition, the epoxy compound may be produced, for example, as shown in the following Formula (13), using a method in which an alcohol having a structure corresponding to the terminal group represented by $R^1$ or $R^5$ in Formula (1) and allyl glycidyl ether are subjected to an addition reaction, and the compound obtained by the addition reaction is then oxidized.

In addition, the epoxy compound may be produced, for example, as shown in the following Formula (14), using a method in which an alcohol having a structure corresponding to the terminal group represented by $R^1$ or $R^5$ in Formula (1) is reacted with glycerin diglycidyl ether.

For the epoxy compound, a commercial product may be purchased and used.

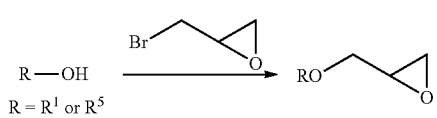

(12)

-continued

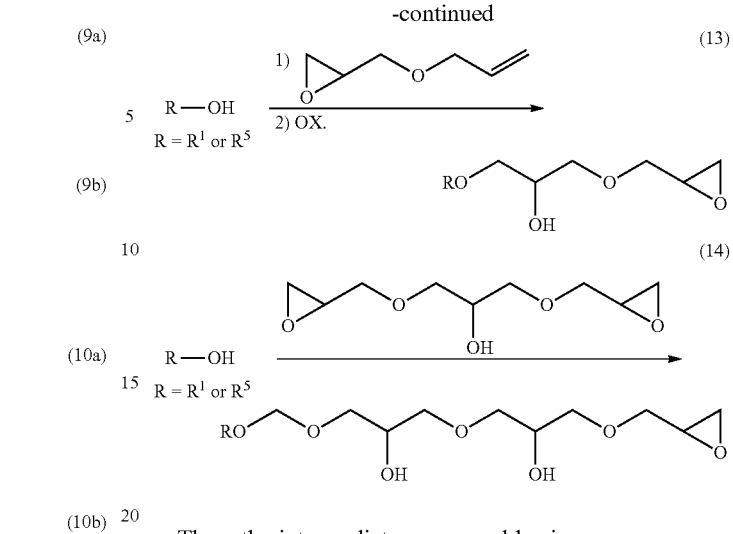

(13)
(14)

Then, the intermediate compound having a group corresponding to $R^1$—$R^2$— at one terminal of the perfluoropolyether chain corresponding to $R^3$ is reacted with epibromohydrin.

By performing the above processes, a compound in which a glycerin structure is provided in the center of the chain structure, and in Formula (1), two PFPE chains represented by $R^3$ are the same, and $R^1$—$R^2$— and $R^5$—$R^4$— are the same is obtained.

(When any One or More of $R^1$ and $R^5$, $R^2$ and $R^4$, and Two PFPE Chains Represented by $R^3$ are Different from Each Other)

In this case also, in the same manner as in the case of producing a compound in which, in Formula (1), two PFPE chains represented by $R^3$ are the same, and $R^1$—$R^2$— and $R^5$—$R^4$— are the same, an intermediate compound having a group corresponding to $R^1$—$R^2$— at one terminal of the perfluoropolyether chain corresponding to $R^3$ is produced.

Next, the intermediate compound having a group corresponding to $R^1$—$R^2$— at one terminal is reacted with epibromohydrin to produce a first intermediate compound having a group corresponding to $R^1$—$R^2$— at one terminal of the perfluoropolyether chain corresponding to $R^3$ and an epoxy group at the other terminal.

Next, in the same manner as the intermediate compound having a group corresponding to $R^1$—$R^2$— at one terminal, a second intermediate compound having a group corresponding to $R^5$—$R^4$— at one terminal of the perfluoropolyether chain corresponding to $R^3$ is produced.

Then, the first intermediate compound is reacted with the second intermediate compound.

By performing the above processes, a compound in which a glycerin structure is provided in the center of the chain structure, and in Formula (1), any one or more of $R^1$ and $R^5$, $R^2$ and $R^4$, and two PFPE chains represented by $R^3$ are different from each other can be produced.

The fluorine-containing ether compound of the present embodiment is a compound represented by Formula (1) in which a glycerin structure is disposed in the center of the chain structure, a PFPE chain represented by $R^3$, a methylene group, divalent linking groups having a polar group represented by $R^2$ and $R^4$, and terminal groups represented by $R^1$ and $R^5$ are bonded in that order to both sides via a methylene group (—$CH_2$—), and at least one terminal group of $R^1$ and $R^5$ is an organic group substituted with a cyano group. Therefore, the lubricating layer formed on the protective layer using the lubricant containing the fluorine-containing ether compound of the present embodiment has excellent adhesion to the protective layer even if the thickness is thin, and has favorable chemical substance resistance and wear resistance.

[Lubricant for Magnetic Recording Medium]

A lubricant for a magnetic recording medium of the present embodiment contains the fluorine-containing ether compound represented by Formula (1).

The lubricant of the present embodiment can be used by being mixed with a known material used as a material for a lubricant as necessary as long as the characteristics of the fluorine-containing ether compound represented by Formula (1) are not impaired due to the inclusion of the known material.

Specific examples of known materials include, for example, FOMBLIN (registered trademark) ZDIAC, FOMBLIN ZDEAL, and FOMBLIN AM-2001 (all commercially available from Solvay Solexis), and Moresco A20H (commercially available from Moresco). A known material used in combination with the lubricant of the present embodiment preferably has a number-average molecular weight of 1,000 to 10,000.

When the lubricant of the present embodiment contains a material other than the fluorine-containing ether compound represented by Formula (1), the content of the fluorine-containing ether compound represented by Formula (1) in the lubricant of the present embodiment is preferably 50 mass % or more, more preferably 60 mass % or more, and still more preferably 70 mass % or more. The upper limit thereof can be arbitrarily selected, and may be, for example, 99 mass % or less, 95 mass % or less, 90 mass % or less, or 80 mass % or less.

Since the lubricant of the present embodiment contains the fluorine-containing ether compound represented by Formula (1), it can cover the surface of the protective layer with high coverage even if the film thickness is thin, and form a lubricating layer having excellent chemical substance resistance and wear resistance.

[Magnetic Recording Medium]

In a magnetic recording medium of the present embodiment, at least a magnetic layer, a protective layer, and a lubricating layer are sequentially provided on a substrate.

In the magnetic recording medium of the present embodiment, as necessary, one, or two or more underlayers can be provided between the substrate and the magnetic layer. In addition, at least one of the adhesive layer and the soft magnetic layer can be provided between the underlayer and the substrate.

The FIG. is a schematic cross-sectional view showing a magnetic recording medium according to one embodiment of the present invention.

A magnetic recording medium 10 of the present embodiment has a structure in which an adhesive layer 12, a soft magnetic layer 13, a first underlayer 14, a second underlayer 15, a magnetic layer 16, a protective layer 17, and a lubricating layer 18 are sequentially provided on a substrate 11.

"Substrate"

As the substrate 11, for example, a non-magnetic substrate in which a film made of NiP or a NiP alloy is formed on a base made of a metal or an alloy material such as Al or an Al alloy can be used.

In addition, as the substrate 11, a non-magnetic substrate made of a non-metal material such as glass, a ceramic, silicon, silicon carbide, carbon, and a resin may be used, or a non-magnetic substrate in which a film of NiP or a NiP alloy is formed on a base made of these non-metal materials may be used.

Since the glass substrate has rigidity and excellent smoothness, it is suitable for increasing the recording density. Examples of glass substrates include an aluminosilicate glass substrate, and a chemically reinforced aluminosilicate glass substrate is particularly suitable.

The roughness of the main surface of the substrate 11 is preferably ultra-smooth with an Rmax of 6 nm or less and an Ra of 0.6 nm or less. Here, the surface roughnesses Rmax and Ra herein are based on the provisions of JIS B0601.

"Adhesive layer"

The adhesive layer 12 prevents the progress of corrosion of the substrate 11 that occurs when the substrate 11 and the soft magnetic layer 13 provided on the adhesive layer 12 are disposed in contact with each other.

The material of the adhesive layer 12 can be appropriately selected from among, for example, Cr, a Cr alloy, Ti, a Ti alloy, CrTi, NiAl, and an AlRu alloy. The adhesive layer 12 can be formed by, for example, a sputtering method.

"Soft Magnetic Layer"

The soft magnetic layer 13 preferably has a structure in which a first soft magnetic film, an intermediate layer made of a Ru film, and a second soft magnetic film are sequentially laminated. That is, the soft magnetic layer 13 preferably has a structure in which an intermediate layer made of a Ru film is interposed between two soft magnetic film layers, and thus the soft magnetic films above and below the intermediate layer are bonded by anti-ferromagnetic coupling (AFC).

Examples of materials of the first soft magnetic film and the second soft magnetic film include a CoZrTa alloy and a CoFe alloy.

It is preferable to add any of Zr, Ta, and Nb to the CoFe alloy used for the first soft magnetic film and the second soft magnetic film. Thereby, the amorphization of the first soft magnetic film and the second soft magnetic film can be promoted, the orientation of the first underlayer (seed layer) can be improved, and the floating height of the magnetic head can be reduced.

The soft magnetic layer 13 can be formed by, for example, a sputtering method.

"First Underlayer"

The first underlayer 14 is a layer that controls the orientation and the crystal size of the second underlayer 15 and the magnetic layer 16 provided thereon.

Examples of the first underlayer 14 include a Cr layer, a Ta layer, a Ru layer, a CrMo alloy layer, a CoW alloy layer, a CrW alloy layer, a CrV alloy layer, and a CrTi alloy layer.

The first underlayer 14 can be formed by, for example, a sputtering method.

"Second Underlayer"

The second underlayer 15 is a layer that controls the orientation of the magnetic layer 16 such that it becomes favorable. The second underlayer 15 is preferably a layer made of Ru or a Ru alloy.

The second underlayer 15 may be a single layer or may be composed of a plurality of layers. When the second underlayer 15 is composed of a plurality of layers, all of the layers may be composed of the same material, or at least one layer may be composed of a different material.

The second underlayer 15 can be formed by, for example, a sputtering method.

"Magnetic Layer"

The magnetic layer 16 is made of a magnetic film in which the axis of easy magnetization is in a direction perpendicular or horizontal to the surface of the substrate.

The magnetic layer 16 is a layer containing Co and Pt, or may be a layer furthermore containing an oxide, Cr, B, Cu, Ta, Zr or the like in order to further improve SNR characteristics.

Examples of oxides contained in the magnetic layer 16 include $SiO_2$, SiO, $Cr_2O_3$, CoO, $Ta_2O_3$, and $TiO_2$.

The magnetic layer 16 may be composed of a single layer or may be composed of a plurality of magnetic layers made of materials with different compositions.

For example, when the magnetic layer 16 is composed of three layers including a first magnetic layer, a second magnetic layer, and a third magnetic layer sequentially laminated from below, the first magnetic layer preferably has a granular structure made of a material containing Co, Cr, and Pt, and further containing an oxide. As the oxide contained in the first magnetic layer, for example, it is preferable to use an oxide of Cr, Si, Ta, Al, Ti, Mg, Co or the like. Among these, particularly, $TiO_2$, $Cr_2O_3$, $SiO_2$ or the like can be preferably used. In addition, the first magnetic layer is preferably made of a composite oxide in which two or more oxides are added. Among these, particularly, $Cr_2O_3$—$SiO_2$, $Cr_2O_3$—$TiO_2$, $SiO_2$—$TiO_2$ or the like can be preferably used.

The first magnetic layer can contain at least one element selected from the group consisting of B, Ta, Mo, Cu, Nd, W, Nb, Sm, Tb, Ru and Re in addition to Co, Cr, Pt, and an oxide.

For the second magnetic layer, the same material as for the first magnetic layer can be used. The second magnetic layer preferably has a granular structure.

The third magnetic layer preferably has a non-granular structure made of a material containing Co, Cr, and Pt, and not containing an oxide. The third magnetic layer can contain at least one element selected from the group consisting of B, Ta, Mo, Cu, Nd, W, Nb, Sm, Tb, Ru, Re and Mn in addition to Co, Cr, and Pt.

When the magnetic layer 16 is formed of a plurality of magnetic layers, it is preferable to provide a non-magnetic layer between adjacent magnetic layers. When the magnetic layer 16 is composed of three layers including a first magnetic layer, a second magnetic layer, and a third magnetic layer, it is preferable to provide a non-magnetic layer between the first magnetic layer and the second magnetic layer, and between the second magnetic layer and the third magnetic layer.

For the non-magnetic layer provided between adjacent magnetic layers of the magnetic layer 16, for example, Ru, a Ru alloy, a CoCr alloy, a CoCrX1 alloy (X1 represents at least one element selected from the group consisting of Pt, Ta, Zr, Re, Ru, Cu, Nb, Ni, Mn, Ge, Si, O, N, W, Mo, Ti, V, Zr and B) or the like can be preferably used.

For the non-magnetic layer provided between adjacent magnetic layers of the magnetic layer 16, it is preferable to use an alloy material containing an oxide, a metal nitride, or a metal carbide. Specifically, as the oxide, for example, $SiO_2$, $Al_2O_3$, $Ta_2O_5$, $Cr_2O_3$, MgO, $Y_2O_3$, $TiO_2$ or the like can be used. As the metal nitride, for example, AlN, $Si_3N_4$, TaN, CrN or the like can be used. As the metal carbide, for example, TaC, BC, SiC or the like can be used.

The non-magnetic layer can be formed by, for example, a sputtering method.

The magnetic layer 16 is preferably a magnetic layer for perpendicular magnetic recording in which the axis of easy magnetization is in a direction perpendicular to the surface of the substrate in order to realize a higher recording density. The magnetic layer 16 may be a magnetic layer for in-plane magnetic recording.

The magnetic layer 16 may be formed by any conventionally known method such as a deposition method, an ion beam sputtering method, and a magnetron sputtering method. The magnetic layer 16 is generally formed by a sputtering method.

"Protective Layer"

The protective layer 17 protects the magnetic layer 16. The protective layer 17 may be composed of one layer or may be composed of a plurality of layers. As the protective layer 17, a carbon-based protective layer can be preferably used, and an amorphous carbon protective layer is particularly preferable. When the protective layer 17 is a carbon-based protective layer, this is preferable because the interaction with the polar group (particularly the hydroxyl group) contained in the fluorine-containing ether compound in the lubricating layer 18 is further improved.

The adhesive force between the carbon-based protective layer and the lubricating layer 18 can be controlled by forming the carbon-based protective layer with hydrogenated carbon and/or nitrogenated carbon and adjusting the hydrogen content and/or the nitrogen content in the carbon-based protective layer. The hydrogen content in the carbon-based protective layer measured by a hydrogen forward scattering method (HFS) is preferably 3 atomic % to 20 atomic %. In addition, the nitrogen content in the carbon-based protective layer measured through X-ray photoelectron spectroscopy (XPS) is preferably 4 atomic % to 15 atomic %.

Hydrogen and/or nitrogen contained in the carbon-based protective layer need not be uniformly contained throughout the entire carbon-based protective layer. For example, the carbon-based protective layer is preferably formed as a composition gradient layer in which nitrogen is contained in the protective layer 17 on the side of the lubricating layer 18 and hydrogen is contained in the protective layer 17 on the side of the magnetic layer 16. In this case, the adhesive force between the magnetic layer 16 and the lubricating layer 18 and the carbon-based protective layer is further improved.

The film thickness of the protective layer 17 is preferably 1 nm to 7 nm. When the film thickness of the protective layer 17 is 1 nm or more, the performance of the protective layer 17 can be sufficiently obtained. The film thickness of the protective layer 17 is preferably 7 nm or less in order to reduce the thickness of the protective layer 17.

As a film forming method for the protective layer 17, a sputtering method using a target material containing carbon, a chemical vapor deposition (CVD) method using a hydrocarbon raw material such as ethylene or toluene, an ion beam deposition (IBD) method or the like can be used.

When a carbon-based protective layer is formed as the protective layer 17, for example, a film can be formed by a DC magnetron sputtering method. In particular, when a carbon-based protective layer is formed as the protective layer 17, it is preferable to form an amorphous carbon protective layer by a plasma CVD method. The amorphous carbon protective layer formed by the plasma CVD method has a uniform surface and low roughness.

"Lubricating layer"

The lubricating layer 18 prevents contamination of the magnetic recording medium 10. In addition, the lubricating layer 18 reduces a frictional force of a magnetic head of a magnetic recording/reproducing device, which slides on the magnetic recording medium 10, and improves the durability of the magnetic recording medium 10.

As shown in the FIG., the lubricating layer 18 is formed on and in contact with the protective layer 17. The lubricating layer 18 is formed by applying the lubricant for a magnetic recording medium of the embodiment described above to the protective layer 17. Therefore, the lubricating layer 18 contains the above fluorine-containing ether compound.

When the protective layer 17 disposed below the lubricating layer 18 is a carbon-based protective layer, the lubricating layer 18 is bonded to the protective layer 17 with a particularly high bonding force. As a result, even if the thickness of the lubricating layer 18 is thin, it is easy to obtain the magnetic recording medium 10 in which the surface of the protective layer 17 is covered with high coverage, and it is possible to effectively prevent contamination of the surface of the magnetic recording medium 10.

The average film thickness of the lubricating layer 18 is preferably 0.5 nm (5 Å) to 2.0 nm (20 Å), and more preferably 0.5 nm (5 Å) to 1.2 nm (12 Å). When the average film thickness of the lubricating layer 18 is 0.5 nm or more, the lubricating layer 18 is formed with a uniform film thickness without forming an island shape or a mesh shape. Therefore, the lubricating layer 18 can cover the surface of the protective layer 17 with high coverage. In addition, when the average film thickness of the lubricating layer 18 is 2.0 nm or less, the lubricating layer 18 can be sufficiently thinned, and the floating height of the magnetic head can be sufficiently reduced.

"Method of Forming Lubricating Layer"

In order to form the lubricating layer 18, for example, a method in which a magnetic recording medium during production in which respective layers up to the protective layer 17 are formed on the substrate 11 is prepared, and a solution for forming a lubricating layer is applied onto the protective layer 17, may be used.

The solution for forming a lubricating layer can be obtained by dispersing and dissolving the lubricant for a magnetic recording medium of the embodiment described above in a solvent as necessary, and adjusting the viscosity and concentration thereof to be suitable for application methods.

Examples of solvents used for the solution for forming a lubricating layer include fluorine-based solvents such as Vertrel (registered trademark) XF (product name, commercially available from Du Pont-Mitsui Fluorochemicals Co., Ltd.).

The method of applying the solution for forming a lubricating layer is not particularly limited, and examples thereof include a spin coating method, a spraying method, a paper coating method, and a dipping method.

When the dipping method is used, for example, the following method can be used. First, the substrate 11 in which respective layers up to the protective layer 17 are formed is immersed in the solution for forming a lubricating layer contained in an immersion vessel of a dip coating device. Next, the substrate 11 is lifted from the immersion vessel at a predetermined speed. Accordingly, the solution for forming a lubricating layer is applied to the surface of the protective layer 17 of the substrate 11.

When the dipping method is used, the solution for forming a lubricating layer can be uniformly applied to the surface of the protective layer 17, and the lubricating layer 18 with a uniform film thickness can be formed on the protective layer 17.

In the present embodiment, it is preferable to heat the substrate 11 on which the lubricating layer 18 is formed. When the heat treatment is performed, the adhesion between the lubricating layer 18 and the protective layer 17 is improved, and the adhesive force between the lubricating layer 18 and the protective layer 17 is improved.

The heat treatment temperature is preferably 100° C. to 180° C., and more preferably 100° C. to 160° C. When the heat treatment temperature is 100° C. or higher, an effect of improving the adhesion between the lubricating layer 18 and the protective layer 17 is sufficiently obtained. In addition, when the heat treatment temperature is 180° C. or lower, it is possible to prevent the thermal decomposition of the lubricating layer 18. The heat treatment time can be appropriately adjusted according to the heat treatment temperature, and is preferably 10 minutes to 120 minutes.

In the present embodiment, in order to further improve the adhesive force of the lubricating layer 18 with respect to the protective layer 17, an ultraviolet ray (UV) irradiating treatment may be performed on the lubricating layer 18 before the heat treatment or after the heat treatment.

In the magnetic recording medium 10 of the present embodiment, at least the magnetic layer 16, the protective layer 17, and the lubricating layer 18 are sequentially provided on the substrate 11. In the magnetic recording medium 10 of the present embodiment, the lubricating layer 18 containing the above fluorine-containing ether compound is formed on and in contact with the protective layer 17. The lubricating layer 18 has excellent adhesion and favorable chemical substance resistance and wear resistance even if the film thickness is thin. Therefore, the magnetic recording medium 10 of the present embodiment has excellent reliability, and particularly has an excellent silicon contamination minimization ability and durability. Therefore, the magnetic recording medium 10 of the present embodiment has a low floating height of the magnetic head (for example, 10 nm or less), and operates stably for a long period of time even in a harsh environment due to diversity of applications. Therefore, the magnetic recording medium 10 of the present embodiment is particularly preferable as a magnetic disk mounted in a load unload (LUL) type magnetic disk device.

EXAMPLES

Hereinafter, the present invention will be described in more detail with reference to examples and comparative examples. Here, the present invention is not limited only to the following examples.

Example 1

The compound represented by Formula (A) was obtained by the following method.

20 g of a compound (a number-average molecular weight of 1,000 and a molecular weight distribution of 1.1) represented by $HOCH_2CF_2O(CF_2CF_2O)_m(CF_2O)CF_2CH_2OH$ (in the formula, m which indicates an average degree of polymerization is 4.5, and n which indicates an average degree of polymerization is 4.5), 2.55 g of a compound represented by Formula (6a), and 20 mL of t-butanol were put into a 100 mL eggplant flask under a nitrogen gas atmosphere, and stirred at room temperature until the composition became uniform to prepare a mixture. 0.90 g of potassium tert-butoxide was added to the mixture, and the mixture was stirred and reacted at 70° C. for 16 hours.

Here, the compound represented by Formula (6a) was synthesized by reacting 2-cyanoethanol and epibromohydrin.

The reaction product obtained after the reaction was cooled to 25° C., transferred to a separatory funnel containing 100 mL of water, and extracted three times with 100 mL of ethyl acetate. The organic layer was washed with water and dehydrated with anhydrous sodium sulfate. After the drying agent was filtered off, the filtrate was concentrated, and the residue was purified by silica gel column chromatography to obtain 8.73 g of a compound represented by the following Formula (15) as an intermediate.

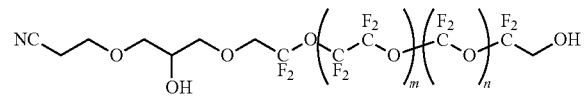

(15)

(in Formula (15), m which indicates an average degree of polymerization is 4.5, and n which indicates an average degree of polymerization is 4.5).

Next, 5.00 g of the compound represented by Formula (15), which was the intermediate obtained above, 0.30 g of epibromohydrin, and 10 mL of t-butanol were put into a 100 mL eggplant flask under a nitrogen gas atmosphere, and stirred at room temperature until the composition became uniform. 0.60 g of potassium tert-butoxide was added to the uniform liquid, and the mixture was stirred and reacted at 70° C. for 23 hours.

The temperature of the reaction solution obtained after the reaction was returned to room temperature, 5 g of a 10% hydrogen chloride/methanol solution (hydrogen chloride-methanol reagent (5-10%) commercially available from Tokyo Chemical Industry Co., Ltd.) was added, and the mixture was stirred at room temperature for 4 hours. Then, the reaction solution was transferred to a separatory funnel containing 100 mL of saline little by little, and extracted twice with 200 mL of ethyl acetate. The organic layer was sequentially washed with 100 mL of saline, 100 mL of saturated sodium bicarbonate water, and 100 mL of saline, and dehydrated with anhydrous sodium sulfate. After the drying agent was filtered off, the filtrate was concentrated, and the residue was purified by silica gel column chromatography to obtain 4.20 g of a compound (A) (in Formula (A), ma1, ma2, na1, and na2 which indicate average degrees of polymerization are 4.5).

$^1$H-NMR and $^{19}$F-NMR measurements of the obtained compound (A) were performed, and the structure was identified from the following results.

$^1$H-NMR (acetone-$D_6$): δ [ppm]=3.40 to 3.60 (4H), 3.65 to 3.85 (8H), 3.85 to 4.10 (19H)

$^{19}$F-NMR (acetone-$D_6$): δ [ppm]=−55.5 to −51.5 (18F), −78.5 (4F), −80.5 (4F), −91.0 to −88.5 (36F)

Example 2

The compound represented by Formula (B) was obtained by the following method.

The compound represented by Formula (15) was reacted with epibromohydrin to obtain a compound represented by the following Formula (16) as an intermediate.

(in Formula (16), m which indicates an average degree of polymerization is 4.5, and n which indicates an average degree of polymerization is 4.5).

20 g of a compound (a number-average molecular weight of 1,000 and a molecular weight distribution of 1.1) represented by $HOCH_2CF_2O(CF_2CF_2O)_m(CF_2O)_nCF_2CH_2OH$ (in the formula, m which indicates an average degree of polymerization is 4.5, and n which indicates an average degree of polymerization is 4.5), 5.70 g of a compound represented by the following Formula (6ba), and 20 mL of t-butanol were put into a 100 mL eggplant flask under a nitrogen gas atmosphere, and stirred at room temperature until the composition became uniform to prepare a mixture. 0.90 g of potassium tert-butoxide was added to the mixture, and the mixture was stirred and reacted at 70° C. for 16 hours.

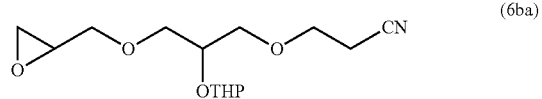

(6ba)

(in Formula (6ba), THP represents a tetrahydropyranyl group).

Here, the compound represented by Formula (6ba) was synthesized using the following method. First, a compound having a cyano group and a hydroxyl group was synthesized by reacting 2-cyanoethanol and allyl glycidyl ether. Then, the secondary hydroxyl group of the obtained compound having a cyano group and a hydroxyl group was protected using dihydropyran, and the double bond was oxidized to obtain an epoxy compound having a cyano group represented by Formula (6ba).

The reaction product obtained after the reaction was cooled to 25° C., transferred to a separatory funnel containing 100 mL of water, and extracted three times with 100 mL of ethyl acetate. The organic layer was washed with water and dehydrated with anhydrous sodium sulfate. After the drying agent was filtered off, the filtrate was concentrated, and the residue was purified by silica gel column chromatography to obtain 17.5 g of a compound represented by the following Formula (17) as an intermediate.

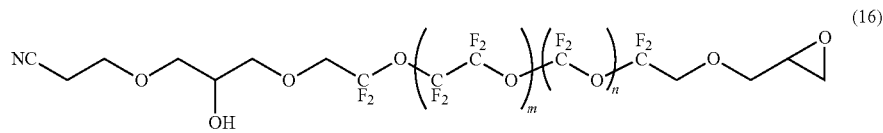

(16)

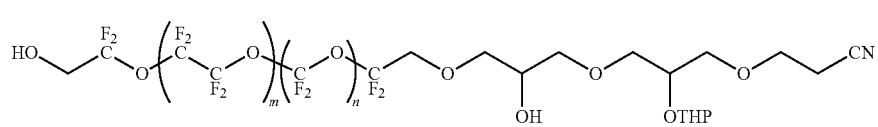

(17)

(in Formula (17), m which indicates the average degree of polymerization is 4.5, n which indicates the average degree of polymerization is 4.5. THP represents a tetrahydropyranyl group).

Next, 10.0 g of the compound represented by Formula (16), 10.2 g of the compound represented by Formula (17), and 20 mL of t-butanol were put into a 100 mL eggplant flask under a nitrogen gas atmosphere, and stirred at room temperature until the composition became uniform. 0.3 g of potassium tert-butoxide was added to the uniform liquid, and the mixture was stirred and reacted at 70° C. for 22 hours.

The temperature of the reaction solution obtained after the reaction was returned to room temperature, 20 g of a 10% hydrogen chloride/methanol solution (hydrogen chloride-methanol reagent (5-10%) commercially available from Tokyo Chemical Industry Co., Ltd.) was added, and the mixture was stirred at room temperature for 4 hours. The reaction solution was transferred to a separatory funnel containing 100 mL of saline little by little, and extracted twice with 200 mL of ethyl acetate. The organic layer was sequentially washed with 100 mL of saline, 100 mL of saturated sodium bicarbonate water, and 100 mL of saline, and dehydrated with anhydrous sodium sulfate. After the drying agent was filtered off, the filtrate was concentrated, and the residue was purified by silica gel column chromatography to obtain 13.5 g of a compound (B) (in Formula (B), mb1, mb2, nb1, and nb2 which indicate average degrees of polymerization are 4.5).

$^1$H-NMR and $^{19}$F-NMR measurements of the obtained compound (B) were performed, and the structure was identified from the following results.

$^1$H-NMR (acetone-$D_6$): δ [ppm]=3.40 to 3.60 (4H), 3.65 to 3.85 (8H), 3.85 to 4.10 (24H)

$^{19}$F-NMR (acetone-$D_6$): δ [ppm]=−55.5 to −51.5 (18F), −78.5 (4F), −80.5 (4F), −91.0 to −88.5 (36F)

Example 3

The compound represented by Formula (C) was obtained by the following method.

The same operation as in Example 2 was performed except that the compound represented by the following Formula (6ca) was used in place of the compound represented by Formula (6ba) in Example 2 to obtain 8.5 g of a compound (C) (in Formula (C), mc1, mc2, nc1, and nc2 which indicate average degrees of polymerization are 4.5).

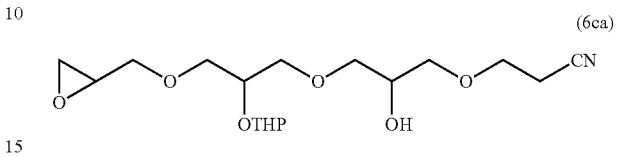

(6ca)

(in Formula (6ca), THP represents a tetrahydropyranyl group).

Here, the compound represented by Formula (6ca) was synthesized by protecting the secondary hydroxyl group of glycerin diglycidyl ether using dihydropyran and then performing a mono addition reaction of 2-cyanoethanol.

$^1$H-NMR and $^{19}$F-NMR measurements of the obtained compound (C) were performed, and the structure was identified from the following results.

$^1$H-NMR (acetone-$D_6$): δ [ppm]=3.40 to 3.60 (4H), 3.65 to 3.85 (8H), 3.85 to 4.10 (29H)

$^{19}$F-NMR (acetone-$D_6$): δ [ppm]=−55.5 to −51.5 (18F), −78.5 (4F), −80.5 (4F), −91.0 to −88.5 (36F)

Example 4

The compound represented by Formula (D) was obtained by the following method.

The same operation as in Example 2 was performed except that epibromohydrin was used in place of the compound represented by Formula (16) in Example 2 to obtain 5.6 g of a compound (D) (in Formula (D), md1, md2, nd1, and nd2 which indicate average degrees of polymerization are 4.5).

$^1$H-NMR and $^{19}$F-NMR measurements of the obtained compound (D) were performed, and the structure was identified from the following results.

$^1$H-NMR (acetone-$D_6$): δ [ppm]=3.40 to 3.60 (4H), 3.65 to 3.85 (8H), 3.85 to 4.10 (29H)

$^{19}$F-NMR (acetone-$D_6$): δ [ppm]=−55.5 to −51.5 (18F), −78.5 (4F), −80.5 (4F), −91.0 to −88.5 (36F)

Example 5

The compound represented by Formula (E) was obtained by the following method.

The compound represented by Formula (17) was reacted with epibromohydrin to obtain a compound represented by the following Formula (18) as an intermediate.

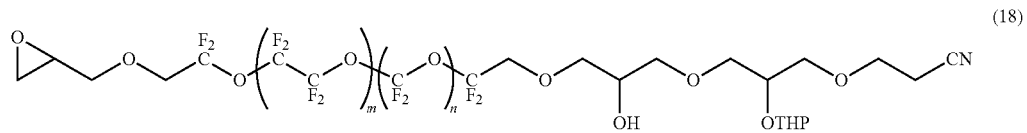

(18)

(in Formula (18), m which indicates an average degree of polymerization is 4.5, and n which indicates an average degree of polymerization is 4.5. THP represents a tetrahydropyranyl group).

The same operation as in Example 2 was performed except that the compound represented by Formula (18) was used in place of the compound represented by Formula (16) and the compound represented by Formula (6ca) was used in place of the compound represented by Formula (6ba) in Example 2 to obtain 6.2 g of a compound (E) (in Formula (E), me1, me2, ne1, and ne2 which indicate average degrees of polymerization are 4.5).

$^1$H-NMR and $^{19}$F-NMR measurements of the obtained compound (E) were performed, and the structure was identified from the following results.

$^1$H-NMR (acetone-D$_6$): δ [ppm]=3.40 to 3.60 (4H), 3.65 to 3.85 (8H), 3.85 to 4.10 (34H)

$^{19}$F-NMR (acetone-D$_6$): δ [ppm]=−55.5 to −51.5 (18F), −78.5 (4F), −80.5 (4F), −91.0 to −88.5 (36F)

Example 6

The compound represented by Formula (F) was obtained by the following method.

The same operation as in Example 1 was performed except that the compound represented by Formula (8ba) was used in place of the compound represented by Formula (6a) in Example 1 to obtain 5.1 g of a compound (F) (in Formula (F), mf1, mf2, nf1, and nf2 which indicate average degrees of polymerization are 4.5).

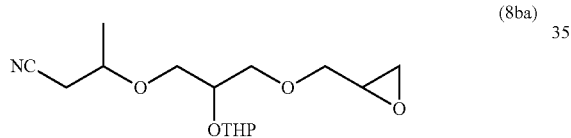

(8ba)

(in Formula (8ba), THP represents a tetrahydropyranyl group).

Here, the compound represented by Formula (8ba) was synthesized using the following method. First, a compound having a cyano group and a hydroxyl group was synthesized by an addition reaction of 3-hydroxybutyronitrile and allyl glycidyl ether. Then, the secondary hydroxyl group of the obtained compound having a cyano group and a hydroxyl group was protected using dihydropyran, and the double bond was oxidized to obtain an epoxy compound having a cyano group represented by Formula (8ba).

$^1$H-NMR and $^{19}$F-NMR measurements of the obtained compound (F) were performed, and the structure was identified from the following results.

$^1$H-NMR (acetone-D$_6$): δ [ppm]=1.50 (6H), 3.40 to 3.60 (4H), 3.65 to 3.85 (6H), 3.85 to 4.10 (29H)

$^{19}$F-NMR (acetone-D$_6$): δ [ppm]=−55.5 to −51.5 (18F), −78.5 (4F), −80.5 (4F), −91.0 to −88.5 (36F)

Example 7

The compound represented by Formula (G) was obtained by the following method.

The same operation as in Example 1 was performed except that the compound represented by Formula (9ba) was used in place of the compound represented by Formula (6a) in Example 1 to obtain 4.9 g of a compound (G) (in Formula (G), mg1, mg2, ng1, and ng2 which indicate average degrees of polymerization are 4.5).

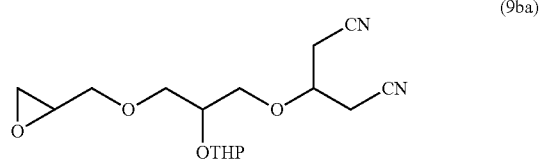

(9ba)

(in Formula (9ba), THP represents a tetrahydropyranyl group).

Here, the compound represented by Formula (9ba) was synthesized using the following method. First, a compound having a cyano group and a hydroxyl group was synthesized by an addition reaction of 3-hydroxyglutaronitrile and allyl glycidyl ether. Then, the secondary hydroxyl group of the obtained compound having a cyano group and a hydroxyl group was protected using dihydropyran, and the double bond was oxidized to obtain an epoxy compound having a cyano group represented by Formula (9ba).

$^1$H-NMR and $^{19}$F-NMR measurements of the obtained compound (G) were performed, and the structure was identified from the following results.

$^1$H-NMR (acetone-D$_6$): δ [ppm]=3.40 to 3.60 (8H), 3.65 to 3.85 (6H), 3.85 to 4.10 (29H)

$^{19}$F-NMR (acetone-D$_6$): δ [ppm]=−55.5 to −51.5 (18F), −78.5 (4F), −80.5 (4F), −91.0 to −88.5 (36F)

Example 8

The compound represented by Formula (H) was obtained by the following method.

The same operation as in Example 1 was performed except that the compound represented by Formula (7a) was used in place of the compound represented by Formula (6a) in Example 1 to obtain 5.3 g of a compound (H) (in Formula (H), mh1, mh2, nh1, and nh2 which indicate average degrees of polymerization are 4.5).

Here, the compound represented by Formula (7a) used in the reaction was synthesized by oxidizing allyl cyanoacetate with m-chloroperoxybenzoic acid.

$^1$H-NMR and $^{19}$F-NMR measurements of the obtained compound (H) were performed, and the structure was identified from the following results.

$^1$H-NMR (acetone-D$_6$): δ [ppm]=3.40 to 3.60 (4H), 3.75 to 4.10 (23H)

$^{19}$F-NMR (acetone-D$_6$): δ [ppm]=−55.5 to −51.5 (18F), −78.5 (4F), −80.5 (4F), −91.0 to −88.5 (36F)

Example 9

The compound represented by Formula (I) was obtained by the following method.

The same operation as in Example 1 was performed except that the compound represented by Formula (10ba) was used in place of the compound represented by Formula (6a) in Example 1 to obtain 5.2 g of a compound (I) (in Formula (I), mi1, mi2, ni1, and ni2 which indicate average degrees of polymerization are 4.5).

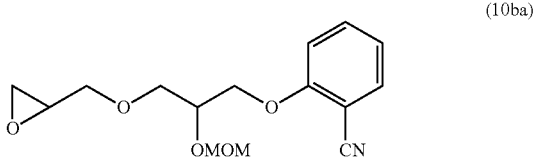

(10ba)

(in Formula (10ba), MOM represents a methoxymethyl group).

Here, the compound represented by Formula (10ba) was synthesized using the following method. First, a compound having a cyano group and a hydroxyl group was synthesized by reacting 2-cyanophenol and allyl glycidyl ether. Then, the secondary hydroxyl group of the obtained compound having a cyano group and a hydroxyl group was protected using chloromethyl methyl ether and the double bond was oxidized to obtain an epoxy compound having a cyano group represented by Formula (10ba).

$^1$H-NMR and $^{19}$F-NMR measurements of the obtained compound (I) were performed, and the structure was identified from the following results.

$^1$H-NMR (acetone-D$_6$): δ [ppm]=3.60 to 3.90 (25H), 4.00 to 4.10 (8H), 7.00 to 7.50 (8H)

$^{19}$F-NMR (acetone-D$_6$): δ [ppm]=−55.5 to −51.5 (18F), −78.5 (4F), −80.5 (4F), −91.0 to −88.5 (36F)

Example 10

The compound represented by Formula (J) was obtained by the following method.

The same operation as in Example 5 was performed except that the compound represented by Formula (9ba) was used in place of the compound represented by Formula (6ca) in Example 5 to obtain 5.0 g of a compound (J) (in Formula (J), mj1, mj2, nj1, and nj2 which indicate average degrees of polymerization are 4.5).

$^1$H-NMR and $^{19}$F-NMR measurements of the obtained compound (J) were performed, and the structure was identified from the following results.

$^1$H-NMR (acetone-D$_6$): δ [ppm]=3.40 to 3.60 (6H), 3.65 to 3.85 (7H), 3.85 to 4.10 (29H)

$^{19}$F-NMR (acetone-D$_6$): δ [ppm]=−55.5 to −51.5 (18F), −78.5 (4F), −80.5 (4F), −91.0 to −88.5 (36F)

Example 11

The compound represented by Formula (K) was obtained by the following method.

The same operation as in Example 5 was performed except that the compound represented by Formula (10a) was used in place of the compound represented by Formula (6ca) in Example 5 to obtain 6.5 g of a compound (K) (in Formula (K), mk1, mk2, nk1, and nk2 which indicate average degrees of polymerization are 4.5).

$^1$H-NMR and $^{19}$F-NMR measurements of the obtained compound (K) were performed, and the structure was identified from the following results.

$^1$H-NMR (acetone-D$_6$): δ [ppm]=3.40 to 3.60 (2H), 3.60 to 3.90 (22H), 4.00 to 4.10 (8H), 7.00 to 7.50 (4H)

$^{19}$F-NMR (acetone-D$_6$): δ [ppm]=−55.5 to −51.5 (18F), −78.5 (4F), −80.5 (4F), −91.0 to −88.5 (36F)

Example 12

The compound represented by Formula (L) was obtained by the following method.

The same operation as in Example 5 was performed except that the compound represented by Formula (19) was used in place of the compound represented by Formula (6ca) in Example 5 to obtain 5.5 g of a compound (L) (in Formula (L), ml1, ml2, nl1, and nl2 which indicate average degrees of polymerization are 4.5).

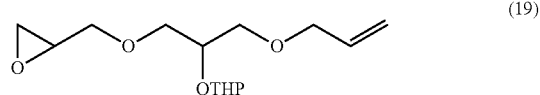

(19)

(in Formula (19), THP represents a tetrahydropyranyl group).

Here, the compound represented by Formula (19) was synthesized by the method described below. The secondary hydroxyl group of glycerin diallyl ether was protected using dihydropyran, and one double bond thereof was oxidized to obtain an epoxy compound having an allyl group represented by Formula (19).

$^1$H-NMR and $^{19}$F-NMR measurements of the obtained compound (L) were performed, and the structure was identified from the following results.

$^1$H-NMR (acetone-D$_6$): δ [ppm]=3.10 (2H), 3.40 to 3.60 (4H), 3.65 to 3.85 (25H), 3.85 to 4.10 (8H), 6.90 (2H), 7.25 (1H)

$^{19}$F-NMR (acetone-D$_6$): δ [ppm]=−55.5 to −51.5 (18F), −78.5 (4F), −80.5 (4F), −91.0 to −88.5 (36F)

Example 13

The compound represented by Formula (M) was obtained by the following method.

The same operation as in Example 5 was performed except that the compound represented by Formula (20) was used in place of the compound represented by Formula (6ca) in Example 5 to obtain 4.5 g of a compound (M) (in Formula (M), mm1, mm2, nm1, and nm2 which indicate average degrees of polymerization are 4.5).

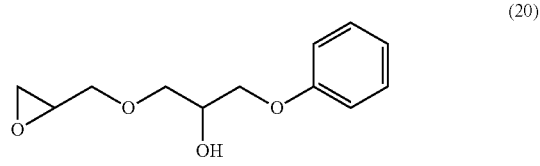 [SMILES: OC(COCC1CO1)COc1ccccc1]

(20)

Here, the compound represented by Formula (20) was synthesized by the method described below. First, a compound having a phenyl group was synthesized by an addition reaction of phenol and allyl glycidyl ether, and the double bond thereof was oxidized to obtain an epoxy compound having a phenyl group represented by Formula (20).

$^1$H-NMR and $^{19}$F-NMR measurements of the obtained compound (M) were performed, and the structure was identified from the following results.

$^1$H-NMR (acetone-D$_6$): δ [ppm]=3.40 to 3.60 (2H), 3.60 to 3.90 (27H), 4.00 to 4.10 (8H), 6.90 (5H)

$^{19}$F-NMR (acetone-$D_6$): δ [ppm]=−55.5 to −51.5 (18F), −78.5 (4F), −80.5 (4F), −91.0 to −88.5 (36F)

Example 14

The compound represented by Formula (N) was obtained by the following method.

The same operation as in Example 5 was performed except that the compound represented by Formula (21) was used in place of the compound represented by Formula (6ca) in Example 5 to obtain 4.2 g of a compound (N) (in Formula (N), mn1, mn2, nm1, nn1 and nn2 which indicate average degrees of polymerization are 4.5).

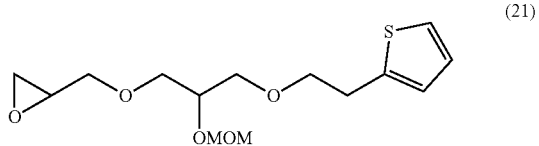

(21)

(in Formula (21), MOM represents a methoxymethyl group).

Here, the compound represented by Formula (21) was synthesized by the method described below. 2-Thiopheneethanol and epibromohydrin were reacted to synthesize a compound, and the obtained compound was hydrolyzed. The primary hydroxyl group of the obtained hydrolyzed compound was protected using a tert-butyldimethylsilyl group and the secondary hydroxyl group thereof was protected using a methoxymethyl group. The tert-butyldimethylsilyl group was deprotected from the obtained compound, and the generated primary hydroxyl group was reacted with epibromohydrin to obtain the epoxy compound having a thienylethyl group represented by Formula (21).

1H-NMR and $^{19}$F-NMR measurements of the obtained compound (N) were performed, and the structure was identified from the following results.

$^1$H-NMR (acetone-$D_6$): δ [ppm]=3.10 (2H), 3.40 to 3.60 (4H), 3.65 to 3.85 (28H), 3.85 to 4.10 (7H), 6.90 (2H), 7.25 (1H)

$^{19}$F-NMR (acetone-$D_6$): δ [ppm]=−55.5 to −51.5 (18F), −78.5 (4F), −80.5 (4F), −91.0 to −88.5 (36F)

Example 15

The compound represented by Formula (D) was obtained by the following method.

The same operation as in Example 1 was performed except that a compound (a number-average molecular weight of 1,000 and a molecular weight distribution of 1.1) represented by $HOCH_2CF_2O(CF_2CF_2O)_{md}(CF_2O)_{nd}CF_2CH_2OH$ (in the formula, md which indicates an average degree of polymerization is 7.0, and nd which indicates an average degree of polymerization is 0) was used in place of the compound (a number-average molecular weight of 1,000 and a molecular weight distribution of 1.1) represented by $HOCH_2CF_2O(CF_2CF_2O)_m(CF_2O)_nCF_2CH_2OH$ (in the formula, m which indicates an average degree of polymerization is 4.5, and n which indicates an average degree of polymerization is 4.5), and the compound represented by Formula (6ba) was used in place of the compound represented by Formula (6a) in Example 1 to obtain 8.5 g of a compound (D) (in Formula (D), md1 and md2 which indicate average degrees of polymerization are 7.0, and nd1 and nd2 which indicate average degrees of polymerization are 0).

$^1$H-NMR and $^{19}$F-NMR measurements of the obtained compound (D) were performed, and the structure was identified from the following results.

$^1$H-NMR (acetone-$D_6$): δ [ppm]=3.40 to 3.60 (4H), 3.65 to 3.85 (8H), 3.85 to 4.10 (29H)

$^{19}$F-NMR (acetone-$D_6$): δ [ppm]=−78.5 (4F), −81.3 (4F), −90.0 to −88.5 (56F)

Example 16

The compound represented by Formula (O) was obtained by the following method.

The same operation as in Example 1 was performed except that a compound (a number-average molecular weight of 1,000 and a molecular weight distribution of 1.1) represented by $HOCH_2CF_2CF_2O(CF_2CF_2CF_2O)_pCF_2CF_2CH_2OH$ (in the formula, p which indicates an average degree of polymerization is 4.5) was used in place of the compound represented by $HOCH_2CF_2O(CF_2CF_2O)_m(CF_2O)_nCF_2CH_2OH$, and the compound represented by Formula (6ba) was used in place of the compound represented by Formula (6a) in Example 1 to obtain 3.4 g of a compound (O) (in Formula (O), po1 and po2 which indicate average degrees of polymerization are each 4.5).

1H-NMR and $^{19}$F-NMR measurements of the obtained compound (O) were performed, and the structure was identified from the following results.

$^1$H-NMR (acetone-$D_6$): δ [ppm]=3.40 to 3.60 (4H), 3.65 to 3.85 (8H), 3.85 to 4.10 (29H)

$^{19}$F-NMR (acetone-$D_6$): δ [ppm]=−84.0 to −83.0 (36F), −86.4 (8F), −124.3 (8F), −130.0 to −129.0 (18F)

Example 17

The compound represented by Formula (P) was obtained by the following method.

The same operation as in Example 1 was performed except that a compound (a number-average molecular weight of 1,000 and a molecular weight distribution of 1.1) represented by $HOCH_2CF_2CF_2CF_2O(CF_2CF_2CF_2CF_2O)_qCF_2CF_2CF_2CH_2OH$ (in the formula, q which indicates an average degree of polymerization is 3.0) was used in place of the compound represented by $HOCH_2CF_2O(CF_2CF_2O)_m(CF_2O)_nCF_2CH_2OH$, and the compound represented by Formula (6ba) was used in place of the compound represented by Formula (6a) in Example 1 to obtain 3.3 g of a compound (P) (in Formula (P), qp1 and qp2 which indicate average degrees of polymerization are each 3.0).

$^1$H-NMR and $^{19}$F-NMR measurements of the obtained compound (P) were performed, and the structure was identified from the following results.

$^1$H-NMR (acetone-$D_6$): δ [ppm]=3.40 to 3.60 (4H), 3.65 to 3.85 (8H), 3.85 to 4.10 (29H)

$^{19}$F-NMR (acetone-$D_6$): δ [ppm]=−84.0 to −83.0 (32F), −122.5 (8F), −126.0 (24F), −129.0 to −128.0 (8F)

Table 1 shows the structure of $R^1$, the structure of $R^2$ (a in Formula (2-1)), the structure of $R^3$ (b and c in Formula (3), d in Formula (4), and e in Formula (5)), the structure of $R^4$ (a in Formula (2-1)), and the structure of $R^5$, when the compounds of Examples 1 to 17 obtained in this manner were applied to Formula (1). In all of the compounds, $Y^2$ in Formula (2-1) representing $R^2$ and $R^4$ is —O—. In addition, in all of the compounds wherein a in Formula (2-1) representing $R^2$ and $R^4$ is 1 or 2, $Y^1$ is —O—.

TABLE 1

| Compound | | $R^1$ | $R^2$ a in Formula (2-1) | $R^3$ | b and c in Formula (3), d in Formula (4), and e in Formula (5) | $R^4$ a in Formula (2-1) | $R^5$ |
|---|---|---|---|---|---|---|---|
| Example 1 | (A) | Formula (6-1) | 0 | Formula (3) | 4.5 | 0 | same as $R^1$ |
| Example 2 | (B) | Formula (6-1) | 0 | Formula (3) | 4.5 | 1 | same as $R^1$ |
| Example 3 | (C) | Formula (6-1) | 0 | Formula (3) | 4.5 | 2 | same as $R^1$ |
| Example 4 | (D) | Formula (6-1) | 1 | Formula (3) | 4.5 | 1 | same as $R^1$ |
| Example 5 | (E) | Formula (6-1) | 1 | Formula (3) | 4.5 | 2 | same as $R^1$ |
| Example 6 | (F) | Formula (8) | 1 | Formula (3) | 4.5 | 1 | same as $R^1$ |
| Example 7 | (G) | Formula (9) | 1 | Formula (3) | 4.5 | 1 | same as $R^1$ |
| Example 8 | (H) | Formula (7) | 0 | Formula (3) | 4.5 | 0 | same as $R^1$ |
| Example 9 | (I) | Formula (10) | 1 | Formula (3) | 4.5 | 1 | same as $R^1$ |
| Example 10 | (J) | Formula (6-1) | 1 | Formula (3) | 4.5 | 1 | Formula (9) |
| Example 11 | (K) | Formula (6-1) | 1 | Formula (3) | 4.5 | 0 | Formula (10) |
| Example 12 | (L) | Formula (6-1) | 1 | Formula (3) | 4.5 | 1 | allyl group |
| Example 13 | (M) | Formula (6-1) | 1 | Formula (3) | 4.5 | 1 | phenyl group |
| Example 14 | (N) | Formula (6-1) | 1 | Formula (3) | 4.5 | 1 | thienylethyl group |
| Example 15 | (D) | Formula (6-1) | 1 | Formula (3) | b = 7.0, c = 0 | 1 | same as $R^1$ |
| Example 16 | (O) | Formula (6-1) | 1 | Formula (4) | 4.5 | 1 | same as $R^1$ |
| Example 17 | (P) | Formula (6-1) | 1 | Formula (5) | 3.0 | 1 | same as $R^1$ |

[Comparative Example 1][Comparative Example 2]

The compound represented by the following Formula (V) was synthesized by the method described in Patent Document 1.

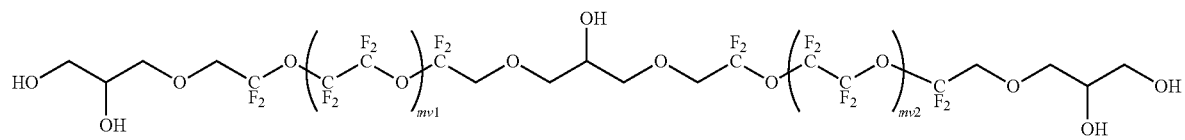

(V)

(in Formula (V), mv1 and mv2 which indicate average degrees of polymerization are 7.0).

[Comparative Example 3][Comparative Example 4]

The compound represented by the following Formula (W) was synthesized by the method described in Patent Document 2.

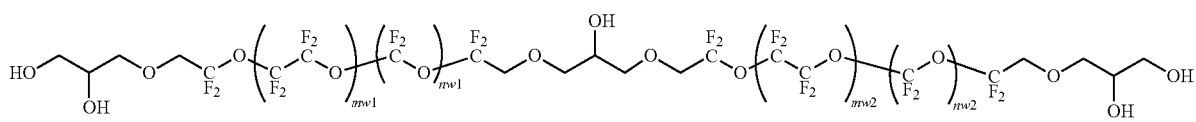

(W)

(in Formula (W), mw1 and mw2, nw1 and nw2 which indicate average degrees of polymerization are 4.5).

[Comparative Example 5][Comparative Example 6]

The compound represented by the following Formula (X) was synthesized by the method described in Patent Document 3.

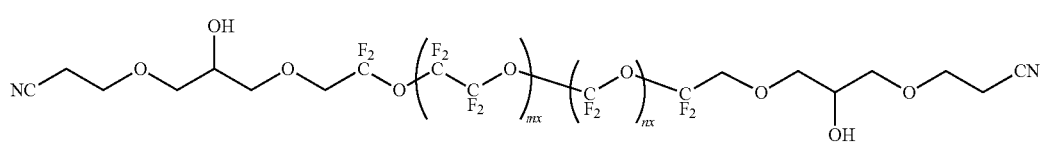

(in Formula (X), mx and nx which indicate average degrees of polymerization are 10.0).

[Comparative Example 7] [Comparative Example 8]

The compound represented by the following Formula (Y) was synthesized by the method described in Patent Document 3.

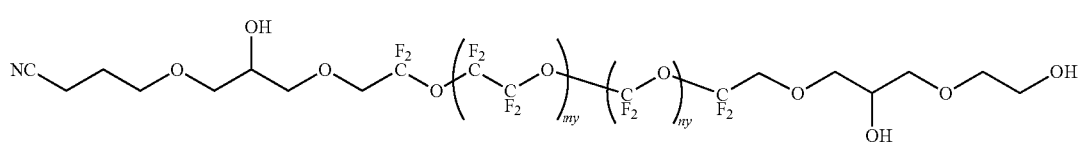

(in Formula (Y), my and ny which indicate average degrees of polymerization are 10.0).

Comparative Example 9

The compound represented by the following Formula (Z) was synthesized by the method described in Patent Document 2.

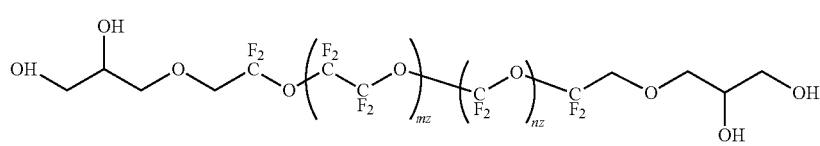

(in Formula (Z), mz and nz which indicate average degrees of polymerization are 10.0).

Next, solutions for forming a lubricating layer were prepared using the compounds obtained in Examples 1 to 17 and Comparative Examples 1 to 9 by the following method. Then, a lubricating layer of a magnetic recording medium was formed using the obtained solution for forming a lubricating layer by the following method to obtain magnetic recording media of Examples 1 to 17 and Comparative Examples 1 to 9.

"Solution for Forming Lubricating Layer"

The compounds obtained in Examples 1 to 17 and Comparative Examples 1 to 9 were dissolved in Vertrel (registered trademark) XF (product name, commercially available from Du Pont-Mitsui Fluorochemicals Co., Ltd.) as a fluorine-based solvent, and diluted with Vertrel XF such that the film thickness became 9.0 Å to 9.5 Å when applied onto the protective layer, and used as solutions for forming a lubricating layer.

"Magnetic Recording Medium"

A magnetic recording medium in which an adhesive layer, a soft magnetic layer, a first underlayer, a second underlayer, a magnetic layer, and a protective layer were sequentially provided on a substrate having a diameter of 65 mm was prepared. The protective layer was made of carbon.

The solutions for forming a lubricating layer of Examples 1 to 17 and Comparative Examples 1 to 9 were applied by a dipping method onto the protective layer of the magnetic recording medium, in which respective layers up to the protective layer were formed. Here, the dipping method was performed under conditions of an immersion speed of 10 mm/sec, an immersion time of 30 sec, and a lifting speed of 1.2 mm/sec.

Then, the magnetic recording medium to which the solution for forming a lubricating layer was applied was put into a thermostatic chamber, a heat treatment for removing the solvent in the solution for forming a lubricating layer and improving the adhesion between the protective layer and the lubricating layer was performed at a thermostatic chamber temperature (heat treatment temperature) shown in Table 2 for 10 minutes, and thus the lubricating layer was formed on the protective layer to obtain a magnetic recording medium.

The film thickness of the lubricating layer of the magnetic recording media of Examples 1 to 17 and Comparative Examples 1 to 9 obtained in this manner was measured using FT-JR (product name: Nicolet iS50, commercially available from Thermo Fisher Scientific). The results are shown in Table 2.

TABLE 2

| | Compound | Number-average molecular weight | Thermostatic chamber temperature (° C.) | Film thickness (Å) | Bond ratio (%) | Wear resistance test | Amount of Si adsorbed | Comprehensive evaluation |
|---|---|---|---|---|---|---|---|---|
| Example 1 | (A) | 2305 | 140 | 9.5 | 60 | A | 0.82 | A |
| Example 2 | (B) | 2379 | 140 | 9.5 | 65 | A | 0.80 | A |
| Example 3 | (C) | 2453 | 140 | 9.0 | 70 | A | 0.64 | A |
| Example 4 | (D) | 2453 | 140 | 9.0 | 70 | A | 0.51 | A |
| Example 5 | (E) | 2527 | 140 | 9.0 | 75 | A | 0.69 | A |
| Example 6 | (F) | 2453 | 140 | 9.0 | 70 | A | 0.59 | A |
| Example 7 | (G) | 2531 | 140 | 9.0 | 70 | A | 0.54 | A |
| Example 8 | (H) | 2361 | 140 | 9.0 | 65 | A | 0.68 | A |
| Example 9 | (I) | 2549 | 140 | 9.0 | 60 | A | 0.68 | A |
| Example 10 | (J) | 2492 | 140 | 9.0 | 70 | A | 0.61 | A |
| Example 11 | (K) | 2427 | 140 | 9.0 | 60 | A | 0.68 | A |
| Example 12 | (L) | 2440 | 140 | 9.0 | 70 | A | 0.68 | A |
| Example 13 | (M) | 2476 | 140 | 9.0 | 70 | A | 0.69 | A |
| Example 14 | (N) | 2510 | 140 | 9.0 | 70 | A | 0.62 | A |
| Example 15 | (D) | 2439 | 140 | 9.0 | 70 | A | 0.70 | A |
| Example 16 | (O) | 2509 | 140 | 9.0 | 70 | A | 0.65 | A |
| Example 17 | (P) | 2511 | 140 | 9.0 | 70 | A | 0.67 | A |
| Comparative Example 1 | (V) | 2184 | 140 | 9.0 | 80 | C | 1.00 | C |
| Comparative Example 2 | (V) | 2184 | 100 | 9.0 | 70 | B | 1.23 | C |
| Comparative Example 3 | (W) | 2198 | 140 | 9.0 | 80 | C | 1.05 | C |
| Comparative Example 4 | (W) | 2198 | 100 | 9.0 | 70 | B | 1.28 | C |
| Comparative Example 5 | (X) | 2252 | 140 | 9.5 | 50 | B | 1.39 | C |
| Comparative Example 6 | (X) | 2252 | 160 | 9.0 | 60 | C | 1.17 | C |
| Comparative Example 7 | (Y) | 2257 | 140 | 9.0 | 55 | B | 1.38 | C |
| Comparative Example 8 | (Y) | 2257 | 160 | 9.0 | 65 | C | 1.25 | C |
| Comparative Example 9 | (Z) | 2146 | 140 | 9.5 | 70 | D | 1.50 | D |

In addition, Table 2 shows the number-average molecular weight (Mn) of the compounds of Examples 1 to 17 and Comparative Examples 1 to 9.

(Measurement of Adhesion Between the Lubricating Layer and the Protective Layer (Bond Ratio))

The magnetic recording medium in which the lubricating layer was formed was washed by a method of immersing it in Vertrel XF as a solvent for 10 minutes, and lifting. The speed at which the magnetic recording medium was immersed in the solvent was 10 mm/sec, and the lifting speed was 1.2 mm/sec.

Then, the film thickness of the lubricating layer was measured by the same method used to measure the film thickness of the lubricating layer before washing.

Then, the film thickness of the lubricating layer before washing was set as A, the film thickness of the lubricating layer after washing (after immersion in the solvent) was set as B, and the binding ratio (bond ratio) of the lubricant was calculated from a ratio of A and B ((B/A)×100(%)). The results are shown in Table 2.

In addition, the following wear resistance test and chemical substance resistance test were performed on the magnetic recording media of Examples 1 to 17 and Comparative Examples 1 to 9.

(Wear Resistance Test)

Using a pin-on disc-type friction wear tester, an alumina sphere having a diameter of 2 mm as a contact was slid on the lubricating layer of the magnetic recording medium at a load of 40 gf and a sliding speed of 0.25 m/sec, and the friction coefficient of the surface of the lubricating layer was measured. Then, the sliding time until the friction coefficient of the surface of the lubricating layer rapidly increased was measured. The sliding time until the friction coefficient rapidly increased was measured four times for the lubricating layer of each magnetic recording medium, and the average value (time) thereof was used as an index of the wear resistance of a lubricant coating.

Table 2 shows the results of the magnetic recording media using the compounds of Examples 1 to 17 and the compounds of Comparative Examples 1 to 9. The evaluation of the wear resistance based on the sliding time until the friction coefficient rapidly increased was as follows.

A (excellent): 650 sec or longer
B (good): 550 sec or longer and shorter than 650 sec
C (acceptable): 450 sec or longer and shorter than 550 sec
D (unacceptable): shorter than 450 sec Here, the time until the friction coefficient rapidly increased could be used as an index of the wear resistance of the lubricating layer for the following reasons. This is because wear of the lubricating layer of the magnetic recording medium proceeds when the magnetic recording medium is used, and when the lubricating layer disappears due to wear, the contact and the protective layer come into direct contact with each other, and the friction coefficient rapidly increases. The time until the friction coefficient rapidly increases is thought to be correlated with the friction test.

(Chemical Substance Resistance Test)

The contamination of the magnetic recording medium due to environmental substances that produced contamination substances in a high temperature environment was examined by the following method. Si ions were used as the environmental substances, and the amount of Si adsorbed was measured as the amount of the contamination substances that contaminated the magnetic recording medium produced from the environmental substances.

Specifically, the magnetic recording medium to be evaluated was held under a high temperature environment with a temperature of 85° C. and a humidity of 0% in the presence of siloxane-based Si rubber for 240 hours. Next, the amount of Si adsorbed present on the surface of the magnetic recording medium was analyzed and measured using secondary-ion mass spectrometry (SIMS), and the degree of contamination with Si ions was evaluated as the amount of Si adsorbed. The amount of Si adsorbed was evaluated using a numerical value which is obtained when the result of Comparative Example 1 was set to 1.00. The results are shown in Table 2.

Then, the magnetic recording media of Examples 1 to 17 and Comparative Examples 1 to 9 were comprehensively evaluated based on the following criteria. The results are shown in Table 2.

A (excellent): The time until the friction coefficient rapidly increased was 650 sec or longer, and the amount of Si adsorbed was less than 0.90

B (good): The time until the friction coefficient rapidly increased was 550 sec or longer and shorter than 650 sec, and the amount of Si adsorbed was 0.90 or more and less than 1.00

C (acceptable): The time until the friction coefficient rapidly increased was 450 sec or longer and shorter than 650 sec, and the amount of Si adsorbed was 1.00 or more and less than 1.40

D (unacceptable): The time until the friction coefficient rapidly increased was shorter than 450 sec, and the amount of Si adsorbed was 1.40 or more As shown in Table 2, all of the magnetic recording media of Examples 1 to 17 had a bond ratio of 60% or more, and had a comprehensive evaluation of "A (excellent)." Accordingly, it was confirmed that the lubricating layers of the magnetic recording media of Examples 1 to 17 had excellent adhesion and favorable chemical substance resistance and wear resistance even if the thickness was thin.

In particular, in Examples 3, 4, 6 and 7 using the compounds wherein the total number of hydroxyl groups contained in the structures of $R^2$ and $R^4$ was 4 and $R^1$ and $R^5$ were any one selected from Formulae (6-1), (8) and (9), and in Examples 10 and 14 using the compounds wherein the total number of hydroxyl groups contained in the structures of $R^2$ and $R^4$ was 4, $R^1$ was Formula (6-1) and $R^5$ was Formula (9) or a thienylethyl group, the bond ratio was 70%, the amount of Si adsorbed was 0.64 or less, and favorable chemical substance resistance and wear resistance were obtained.

In Example 4 using the compound (D), wherein the total number of hydroxyl groups contained in the structures of $R^2$ and $R^4$ was 4 and the number of hydroxyl groups contained in the structure of $R^2$ and that of $R^4$ were the same, the compound has a symmetric structure wherein a glycerin structure is located at the center. Accordingly, it is assumed that the compound of Example 4 easily and uniformly wets and spreads on the protective layer, and compared with Example 3 using the compound (C) wherein the number of hydroxyl groups contained in the structure of $R^2$ was different from that of $R^4$, coating ability became excellent, and a favorable chemical substance resistance was obtained. In addition, Example 4 showed excellent chemical substance resistance, compared with Example 5 using the compound (E) wherein the total number of hydroxyl groups contained in the structures of $R^2$ and $R^4$ was 5. This was speculated to be because Example 4, compared with Example 5, had a smaller number of polar groups which were not involved in binding of the lubricating layer to the active sites on the protective layer, and the attraction of the environmental substances which produce contamination substances, caused by the polar groups which were not involved in binding of the lubricating layer to the active sites on the protective layer, was suppressed.

In addition, based on the results of Examples 1 to 3, it was confirmed that, when a compound having a large total number of hydroxyl groups contained in the structure of $R^2$ and $R^4$ in Formula (1) was used, the bond ratio was high, the adhesion became favorable, the amount of Si adsorbed was small, and the chemical substance resistance became favorable. However, in Example 5 using a compound wherein the total number of hydroxyl groups contained in the structure of $R^2$ and $R^4$ in Formula (1) was 5, the bond ratio thereof was higher than in Example 4 using a compound wherein the total number was 4, but the amount of Si adsorbed was larger. This was speculated to be because the hydroxyl groups which were included in the compound but not involved in binding to the active sites on the protective layer attracted the environmental substances, which produce contamination substances, to the lubricating layer.

On the other hand, in Comparative Examples 1 and 3 using a compound in which a glycerin structure was disposed in the center of the chain structure, a perfluoropolyether chain and a terminal group having two hydroxyl groups were bonded in that order to both sides, and hydroxyl groups were disposed at both end terminals of the chain structure, the bond ratio was 80%, and the adhesion was higher than in Examples 1 to 17. However, in Comparative Examples 1 and 3, since the adhesion was too strong, the lubricity of the lubricating layer was impaired, and the result of the wear resistance test was "C (acceptable)."

In addition, in Comparative Examples 2 and 4 in which the same compounds as in Comparative Examples 1 and 3 was used, and the adhesion was weakened by lowering the heat treatment temperature (thermostatic chamber temperature), the result of the wear resistance test was "B (good)," but the amount of Si adsorbed was large. This was speculated to be because hydroxyl groups which were included in the compound but not involved in binding to the active sites on the protective layer attracted the environmental substances, which produce contamination substances, to the lubricating layer.

In addition, in Comparative Example 5 using a compound in which a perfluoropolyether chain was disposed in the center of the chain structure, terminal groups having one cyano group and one hydroxyl group were disposed at both ends, and the cyano groups were disposed at both end terminals of the chain structure, the bond ratio was 50%, and compared with Examples 1 to 17, adhesion was lower and the amount of Si adsorbed was larger.

In addition, in Comparative Example 7 using a compound in which a perfluoropolyether chain was disposed in the center of the chain structure, a terminal group having two hydroxyl groups was disposed at one end, a terminal group having one cyano group and one hydroxyl group was disposed at the other end, the hydroxyl group was disposed at one end terminal of the chain structure and the cyano group was disposed at the other end terminal thereof, the bond ratio was 55%, and compared with Examples 1 to 17, adhesion was lower and the amount of Si adsorbed was larger.

This was speculated to be because the compounds used in Comparative Examples 5 and 7 did not have a glycerin structure in the center of the chain structure, and therefore an effect of improving the adhesion by the bond between the hydroxyl group disposed in the center of the chain structure and the protective layer was not obtained.

In addition, in Comparative Examples 6 and 8 in which the same compounds as in Comparative Examples 5 and 7 were used, and the adhesion was increased by increasing the heat treatment temperature (thermostatic chamber temperature), the bond ratio was 60% or more, but the result of the wear resistance test was "C (acceptable)".

In addition, in Comparative Example 9 using a compound in which a perfluoropolyether chain was disposed in the center of the chain structure, a terminal group having two hydroxyl groups was bonded to both sides thereof, and hydroxyl groups were disposed at both end terminals of the chain structure, the result of the wear resistance test was "D (unacceptable)," and the amount of Si adsorbed was larger than in Examples 1 to 17.

INDUSTRIAL APPLICABILITY

When the lubricant for a magnetic recording medium containing the fluorine-containing ether compound of the present invention is used, it is possible to form a lubricating layer having excellent adhesion and favorable chemical substance resistance and wear resistance even if the thickness is thin.

REFERENCE SIGNS LIST

10 Magnetic recording medium
11 Substrate
12 Adhesive layer
13 Soft magnetic layer
14 First underlayer
15 Second underlayer
16 Magnetic layer
17 Protective layer
18 Lubricating layer

The invention claimed is:

1. A fluorine-containing ether compound represented by the following Formula (1):

(in Formula (1), $R^3$ represents a perfluoropolyether chain; $R^2$ and $R^4$ represent a divalent linking group having a polar group, and may be the same as or different from each other; $R^1$ and $R^5$ represent a terminal group bonded to an oxygen atom of $R^2$ or $R^4$, and may be the same as or different from each other; and at least one of $R^1$ and $R^5$ is an organic group having 1 to 8 carbon atoms and at least one of hydrogens included in the organic group is substituted by a cyano group).

2. The fluorine-containing ether compound according to claim 1,
wherein the organic group is a phenyl group, or an alkyl group having 1 to 5 carbon atoms.

3. The fluorine-containing ether compound according to claim 1,
wherein the polar group is a hydroxyl group.

4. The fluorine-containing ether compound according to claim 3,
wherein, in Formula (1), a total number of a hydroxyl group contained in $R^2$ and a hydroxyl group contained in $R^4$ is 2 to 5.

5. The fluorine-containing ether compound according to claim 1,
wherein, in Formula (1), $R^2$ and $R^4$ contain 1 to 3 linking groups represented by the following Formula (2):

6. The fluorine-containing ether compound according to claim 5,
wherein, in Formula (1), $R^2$ and $R^4$ are a linking group represented by the following Formula (2-1):

(in Formula (2-1), a represents an integer of 0 to 2; X represents Formula (2); $Y^1$ represents any one selected from the group consisting of —O—, —CH$_2$—, —CH$_2$O—, and —OCH$_2$—; and $Y^2$ represents —O— or —CH$_2$O—).

7. The fluorine-containing ether compound according to claim 6, wherein, in Formula (2-1), $Y^1$ and $Y^2$ are —O—.

8. The fluorine-containing ether compound according to claim 1,
wherein, in Formula (1), $R^3$ is any one selected from the group consisting of perfluoropolyether chains represented by the following Formulae (3) to (5):

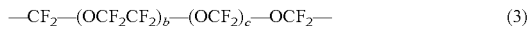

(in Formula (3), b and c indicate an average degree of polymerization, b represents 1 to 20, and c represents 0 to 20),

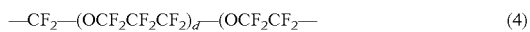

(in Formula (4), d indicates an average degree of polymerization, and represents 1 to 20), and

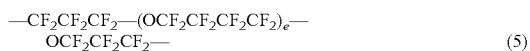

(in Formula (5), e indicates an average degree of polymerization, and represents 1 to 10).

9. The fluorine-containing ether compound according to claim 1,
wherein, in Formula (1), $R^1$ and $R^5$ are a phenyl group which is substituted with at least one cyano group, or an alkyl group having 1 to 5 carbon atoms which is substituted with at least one cyano group.

10. The fluorine-containing ether compound according to claim 1,
wherein, in Formula (1), two perfluoropolyether chains represented by $R^3$ are the same, $R^2$ and $R^4$ are the same, and $R^1$ and $R^5$ are the same.

11. The fluorine-containing ether compound according to claim 1,
wherein, in Formula (1),
one of $R^1$ and $R^5$ is a phenyl group which is substituted with at least one cyano group, or an alkyl group having 1 to 5 carbon atoms which is substituted with at least one cyano group, and
the other of $R^1$ and $R^5$ is an organic group which includes at least one selected from the group consisting of an aromatic hydrocarbon-containing group, an aromatic heterocycle-containing group, an alkenyl group, and an alkynyl group.

12. The fluorine-containing ether compound according to claim 1, which is any of compounds represented by the following Formulae (A) to (P):

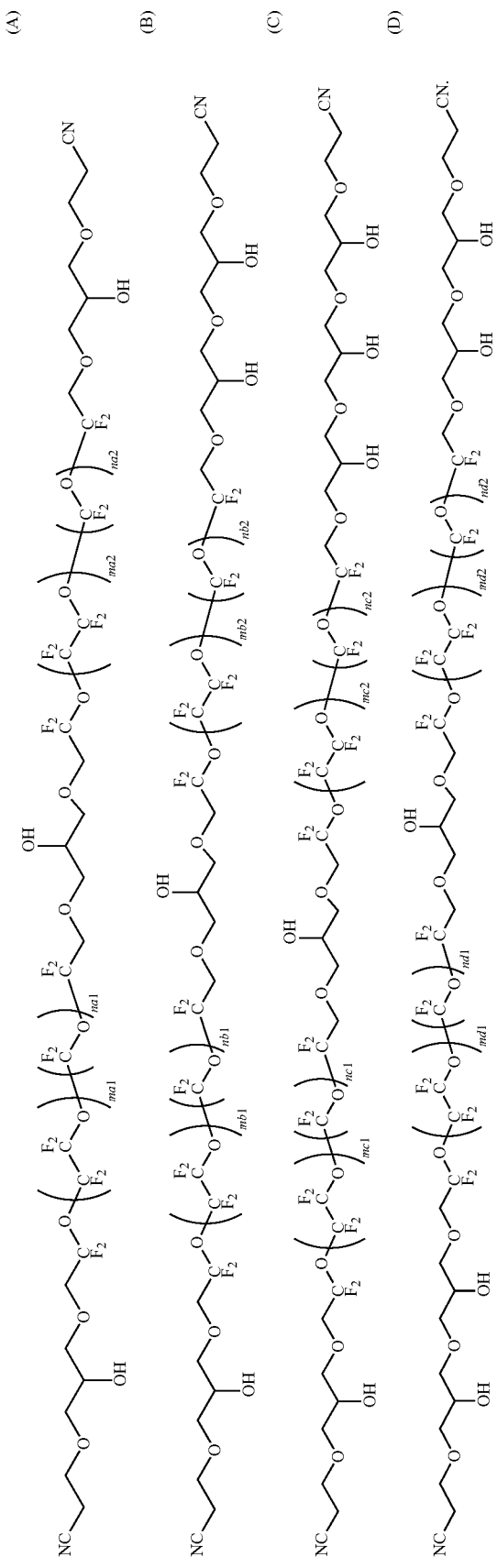

(in Formula (A), ma1, ma2, na1, and na2 indicate an average degree of polymerization, ma1 and ma2 represent 1 to 20, and na1 and na2 represent 0 to 20), (in Formula (B), mb1, mb2, nb1, and nb2 indicate an average degree of polymerization, mb1 and mb2 represent 1 to 20, and nb1 and nb2 represent 0 to 20), in Formula (C), mc1, mc2, nc1, and nc2 indicate an average degree of polymerization, mc1 and mc2 represent 1 to 20, and nc1 and nc2 represent 0 to 20), and (in Formula (D), md1, md2, nd1, and nd2 indicate an average degree of polymerization, md1 and md2 represent 1 to 20, and nd1 and nd2 represent 0 to 20),

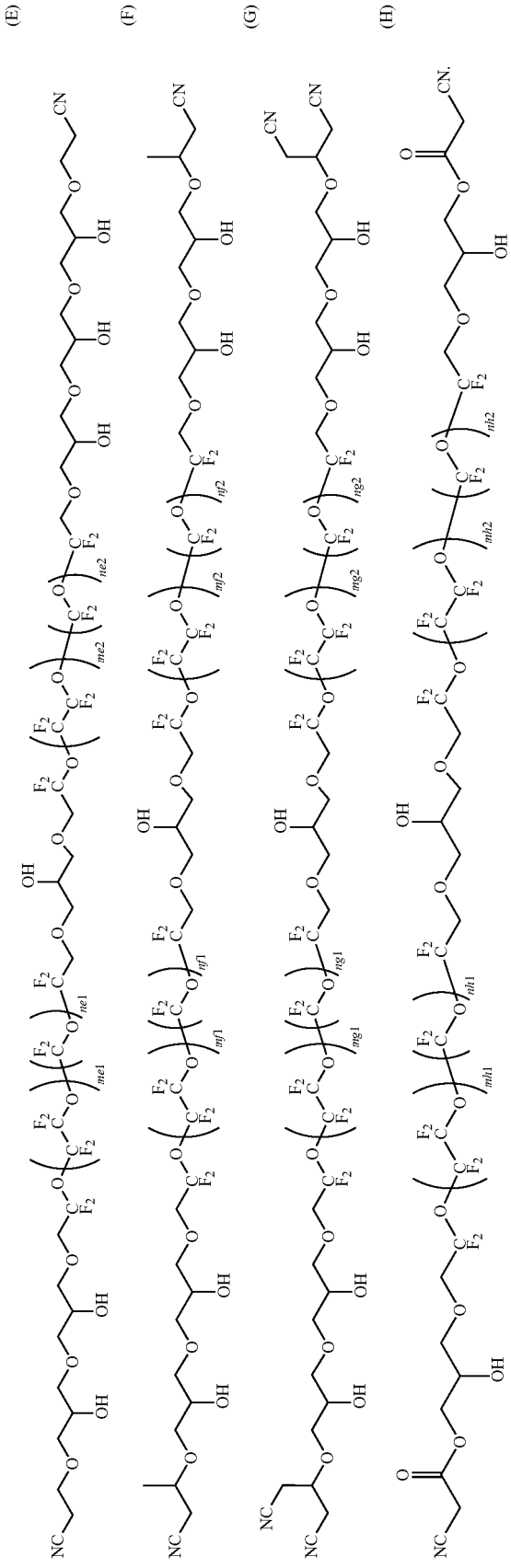

(in Formula (E), me1 me2, ne1, and ne2 indicate an average degree of polymerization, me1 and me2 represent 1 to 20, and ne1 and ne2 represent 0 to 20), (in Formula (F), mf1, mf2, nf1, and nf2 indicate an average degree of polymerization, mf1 and mf2 represent 1 to 20, and nf1 and nf2 represent 0 to 20), (in Formula (G), mg1, mg2, ng1, and ng2 indicate an average degree of polymerization, mg1 and mg2 represent 1 to 20, and ng1 and ng2 represent 0 to 20), and (in Formula (H), mh1, mh2, nh1, and nh2 indicate an average degree of polymerization, mh1 and mh2 represent 1 to 20, and nh1 and nh2 represent 0 to 20),

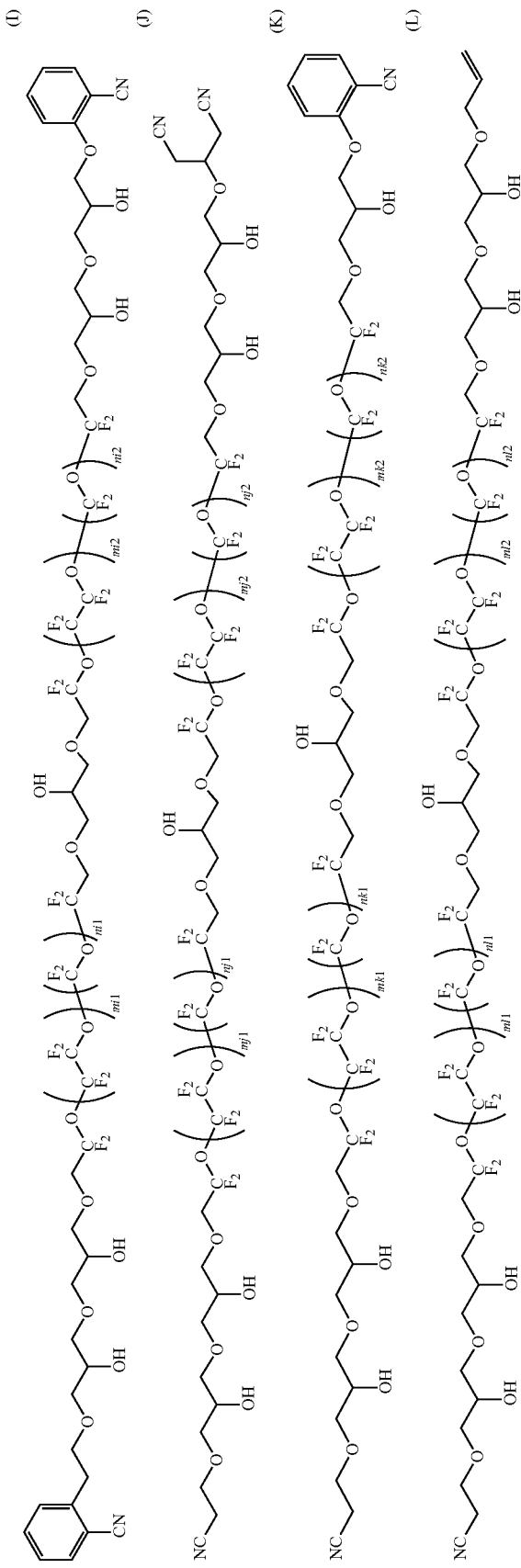

(in Formula (I), mi1, mi2, ni1, and ni2 indicate an average degree of polymerization, mi1 and mi2 represent 1 to 20, and ni1 and ni2 represent 0 to 20), (in Formula (J), mj1, mj2, nj1, and nj2 indicate an average degree of polymerization, mj1 and mj2 represent 1 to 20, and nj1 and nj2 represent 0 to 20), in Formula (K), mk1, mk2, nk1, and nk2 indicate an average degree of polymerization, mk1 and mk2 represent 1 to 20, and nk1 and nk2 represent 0 to 20), and (in Formula (L), ml1, ml2, nl1, and nl2 indicate an average degree of polymerization, ml1 and ml2 represent 1 to 20, and nl1 and nl2 represent 0 to 20),

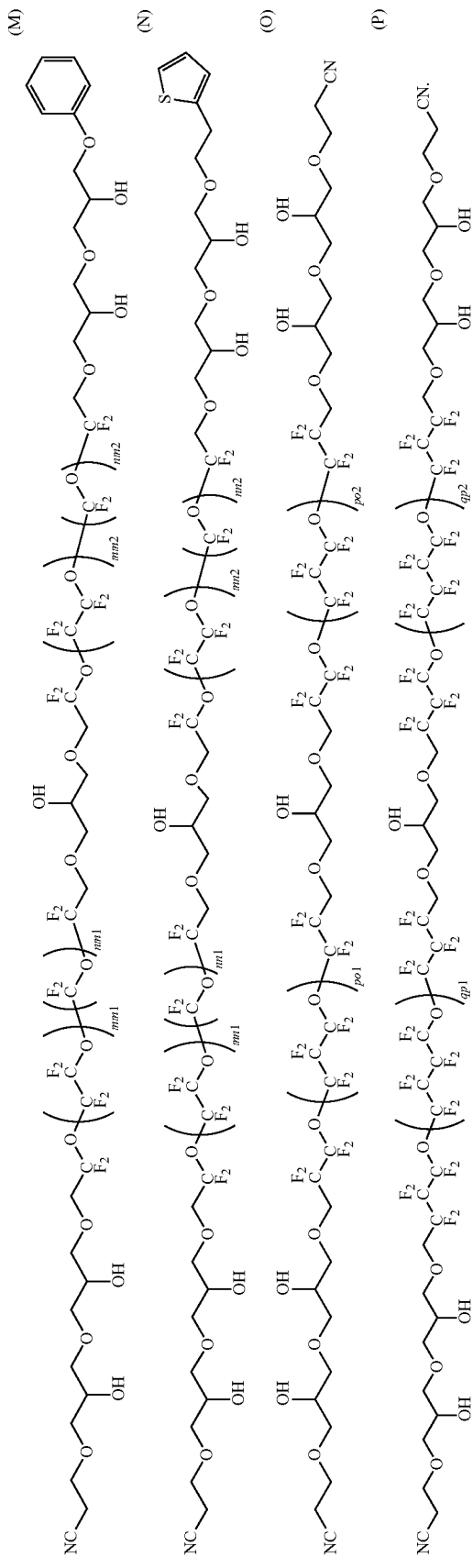

(in Formula (M), mm1, mm2, nm1, and nm2 indicate an average degree of polymerization, mm1 and mm2 represent 1 to 20, and nm1 and nm2 represent 0 to 20), (in Formula (N), mn1, mn2, nn1, and nn2 indicate an average degree of polymerization, mn1 and mn2 represent 1 to 20, and nn1 and nn2 represent 0 to 20), (in Formula (O), po1 and po2 indicate an average degree of polymerization, and each represent 1 to 20), and (in Formula (P), qp1 and qp2 indicate an average degree of polymerization, and each represent 1 to 10).

13. The fluorine-containing ether compound according to claim 1,
wherein the number-average molecular weight thereof is in a range of 500 to 10,000.

14. A lubricant for a magnetic recording medium, which contains the fluorine-containing ether compound according to claim 1.

15. A magnetic recording medium having at least a magnetic layer, a protective layer, and a lubricating layer sequentially provided on a substrate,
wherein the lubricating layer contains the fluorine-containing ether compound according to claim 1.

16. The magnetic recording medium according to claim 15, wherein the average film thickness of the lubricating layer is 0.5 nm to 2.0 nm.

* * * * *